United States Patent
Bellido et al.

(10) Patent No.: US 11,672,811 B2
(45) Date of Patent: Jun. 13, 2023

(54) MATERIALS AND METHODS FOR SUPPRESSING AND/OR TREATING BONE RELATED DISEASES AND SYMPTOMS

(71) Applicants: Indiana University Research and Technology Corporation, Indianapolis, IN (US); University of Rochester, Rochester, NY (US); The United States of America As Represented by the Department of Veterans Affairs Office of General, Washington, DC (US)

(72) Inventors: Teresita M. Bellido, Zionsville, IN (US); G. David Roodman, Indianapolis, IN (US); Jesus Delgado-Calle, Indianapolis, IN (US); Robert K. Boeckman, Honeoye Falls, NY (US); Frank H. Ebetino, Venice, FL (US)

(73) Assignees: Indiana University Research and Technology Corporation, Indianapolis, IN (US); University of Rochester, Rochester, NY (US); The United States of America as Represented by the Department of Veteranas Affairs, Washington, DC (US)

( * ) Notice: Subject to any disclaimer, the term of this patent is extended or adjusted under 35 U.S.C. 154(b) by 37 days.

(21) Appl. No.: 16/635,769

(22) PCT Filed: Aug. 2, 2018

(86) PCT No.: PCT/US2018/045037
§ 371 (c)(1),
(2) Date: Jan. 31, 2020

(87) PCT Pub. No.: WO2019/028270
PCT Pub. Date: Feb. 7, 2019

(65) Prior Publication Data
US 2020/0368259 A1 Nov. 26, 2020

Related U.S. Application Data

(60) Provisional application No. 62/540,396, filed on Aug. 2, 2017.

(51) Int. Cl.
| | | |
|---|---|---|
| *A61K 31/664* | (2006.01) | |
| *A61P 35/00* | (2006.01) | |
| *A61K 38/29* | (2006.01) | |
| *A61K 45/06* | (2006.01) | |
| *C07F 9/38* | (2006.01) | |

(52) U.S. Cl.
CPC ............ *A61K 31/664* (2013.01); *A61K 38/29* (2013.01); *A61K 45/06* (2013.01); *A61P 35/00* (2018.01); *C07F 9/3886* (2013.01)

(58) Field of Classification Search
None
See application file for complete search history.

(56) References Cited

U.S. PATENT DOCUMENTS

2002/0111292 A1 5/2002 Mundy
2011/0288090 A1 11/2011 Armstrong

OTHER PUBLICATIONS

Roderick et al. ("Therapeutic targeting of NOTCH signaling ameliorates immune-mediated bone marrow failure of aplastic anemia"; J. Exp Med (2013) 201(7);1311-1329).*
Xu et al. ("Basic research and clinical application of bisphosphonates in bone disease: what have we learned over the last 40 years" Journal of Translational medicine 11 (2013)).*
Crasto et al. ("Linker: a program to generate linker sequences for fusion proteins" Protein engineering vol. 13 No. 5, pp. 309-312, 2000).*
The Merriam Webster Dictionary (https://www.merriam-webster.com/dictionary/metabolite accessed Dec. 4, 2021).*
Colombo et al. ("Notch-directed microenviroment reprogramming in myeloma: a single path to multiple outcomes" Leukemia (2013) 27, 1009-1018).*
Terpos et al. ("The use of bisphosphonates in multiple myeloma: recommendations of an expert panel on behalf of the European Myeloma Network"Annals of Oncology 20: 1303-1317,2009).*
Xie et al. ("Design, Synthesis and Pharmocokinetics of a Bone-Targeted dual action prodrug for the treatment of osteoporosis"J. Med. Chem 7/12/20170).*
MedChemExpress (https://www.medchemexpress.com/Z-lle-Leu-aldehyde.html accessed Dec. 4, 2021).*
Nie et al. ("γ-Secretase inhibitors and modulators: Mechanistic insights into the function and regulation of γ-Secretase" Semin Cell Dev Biol. Sep. 2020; 105:43-53).*
Written Opinion of the International Searching Authority, dated Nov. 15, 2018, for International Patent Application No. PCT/US2018/045037; 7 pages.
International Search Report issued by the International Searching Authority, dated Nov. 15, 2018, for International Patent Application No. PCT/US2018/045037; 4 pages.

* cited by examiner

*Primary Examiner* — Julie Ha
*Assistant Examiner* — Tara L Martinez
(74) *Attorney, Agent, or Firm* — Faegre Drinker Biddle & Reath LLP

(57) ABSTRACT

Various aspects and embodiments disclosed herein relate generally to the modelling, treatment, reducing resistance to the treatment, prevention, and diagnosis of diseases/symptoms induced by multiple myeloma. Embodiments include methods of treating a bone related disease, comprising the steps of: administering to a subject at least one therapeutically effective dose of a compound disclosed herein.

5 Claims, 18 Drawing Sheets

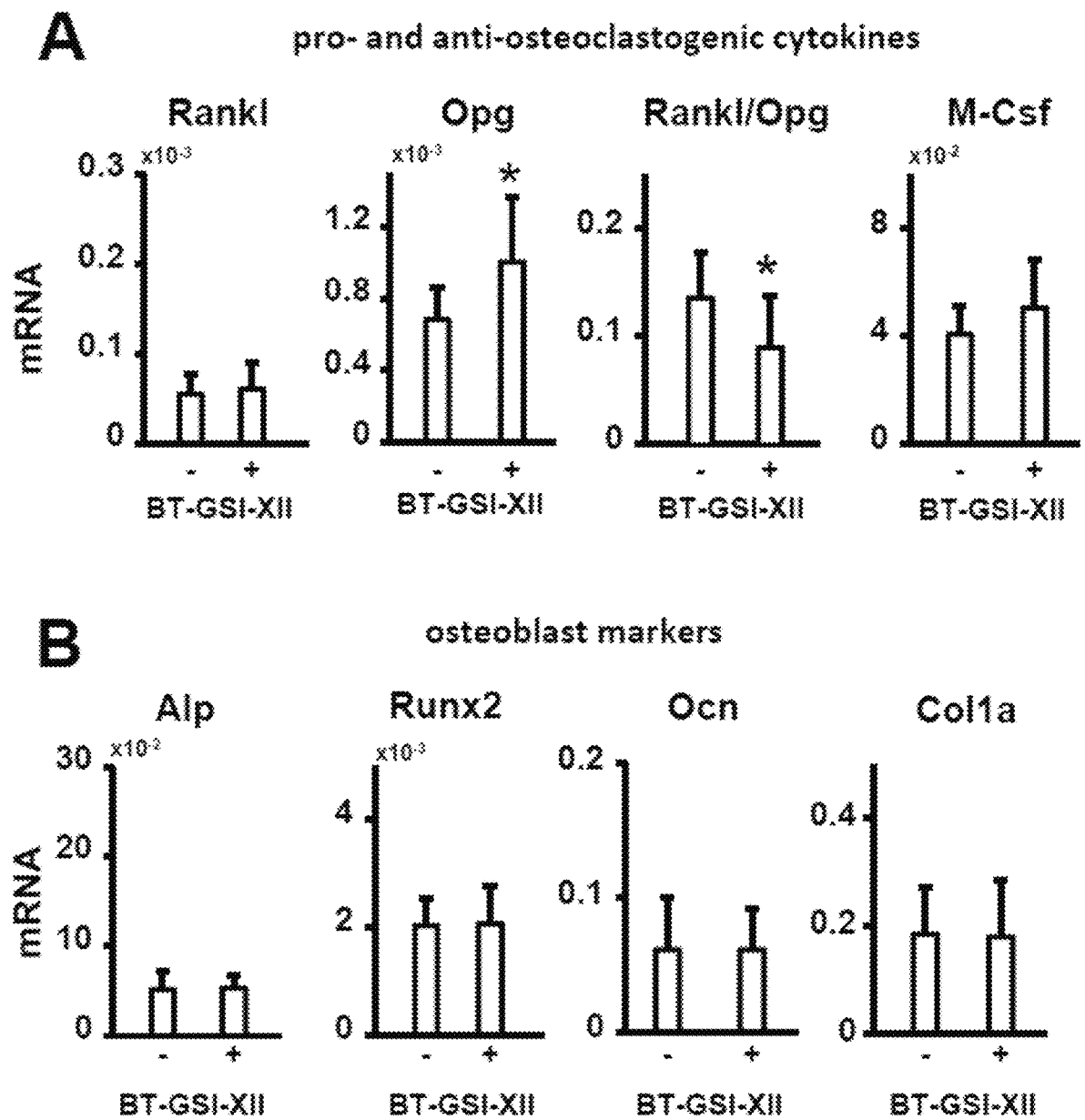
FIG. 3A-B

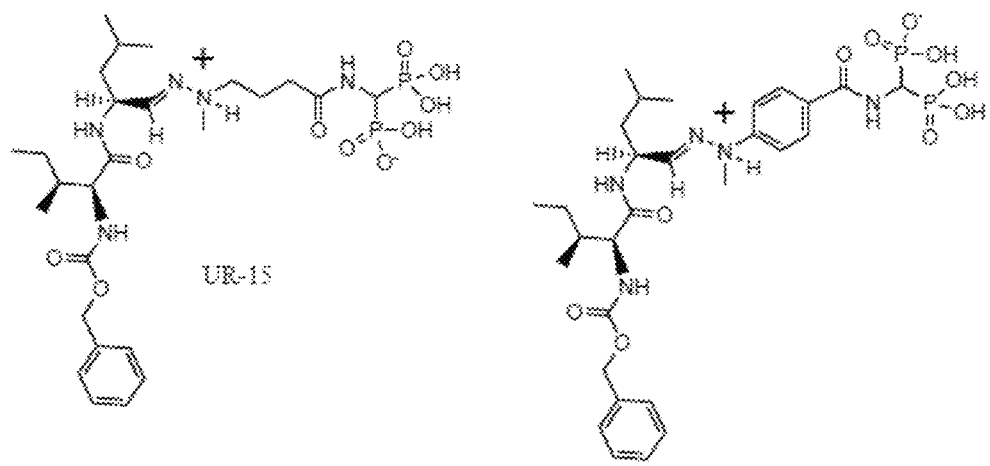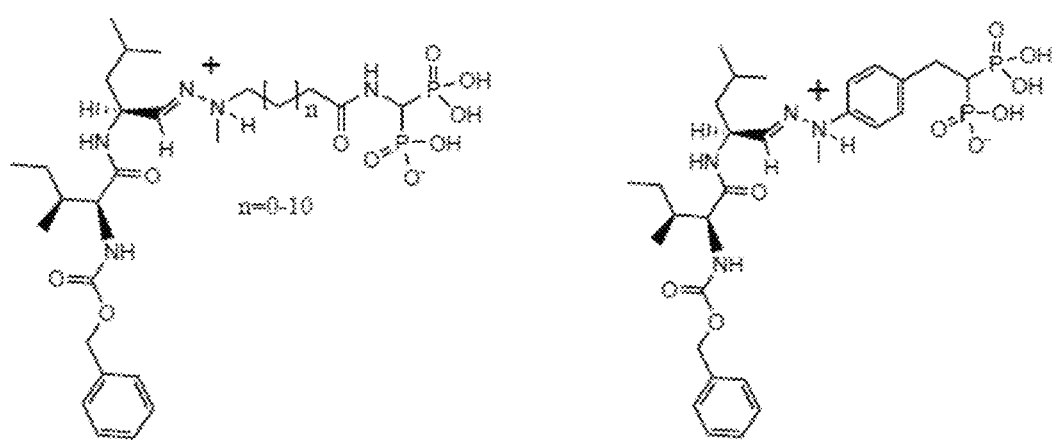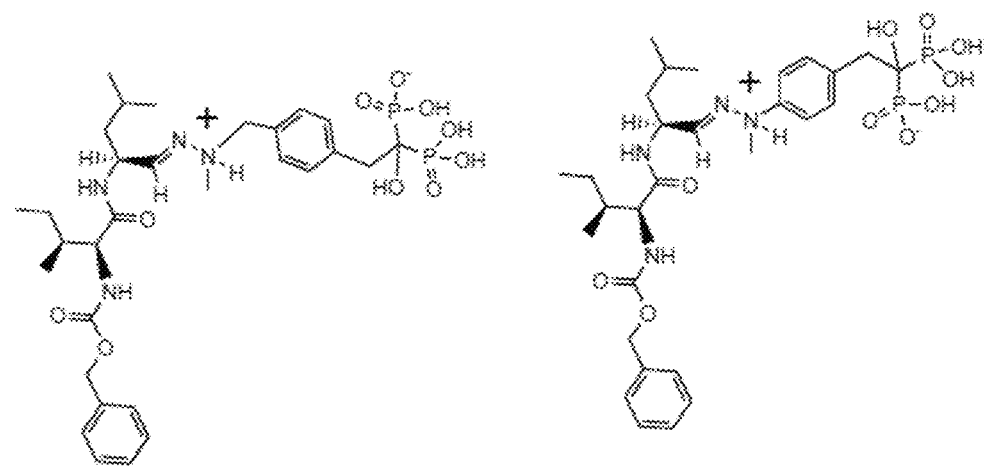
FIG. 4

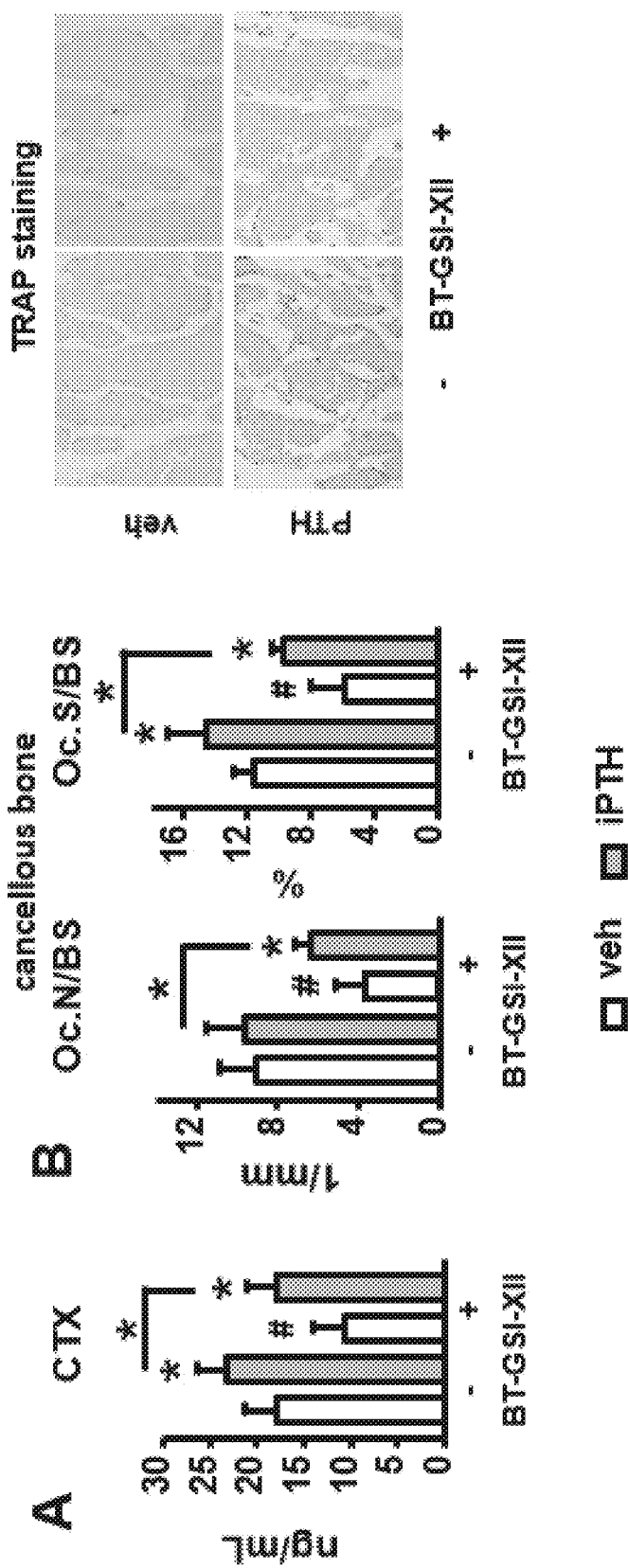
FIG. 12A-B

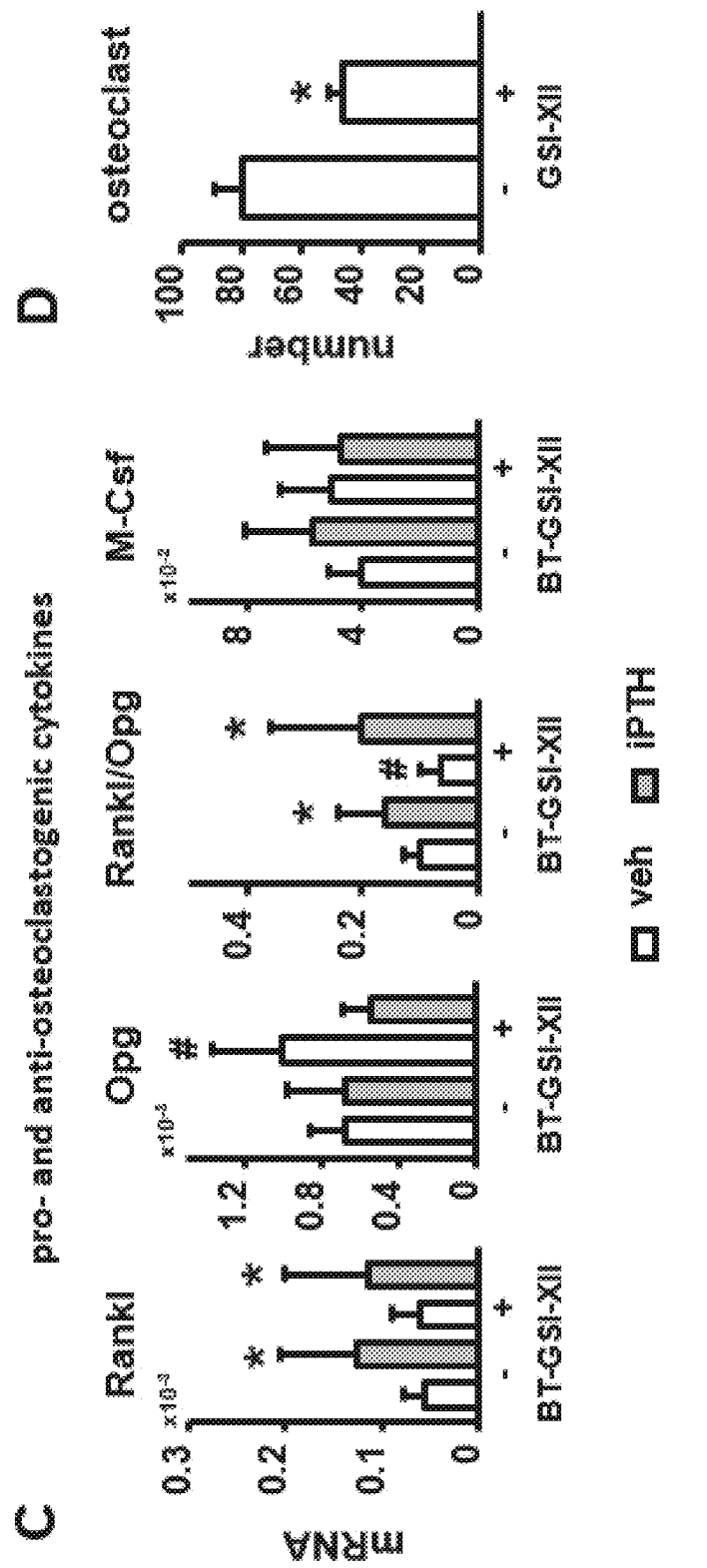
FIG. 12C-D

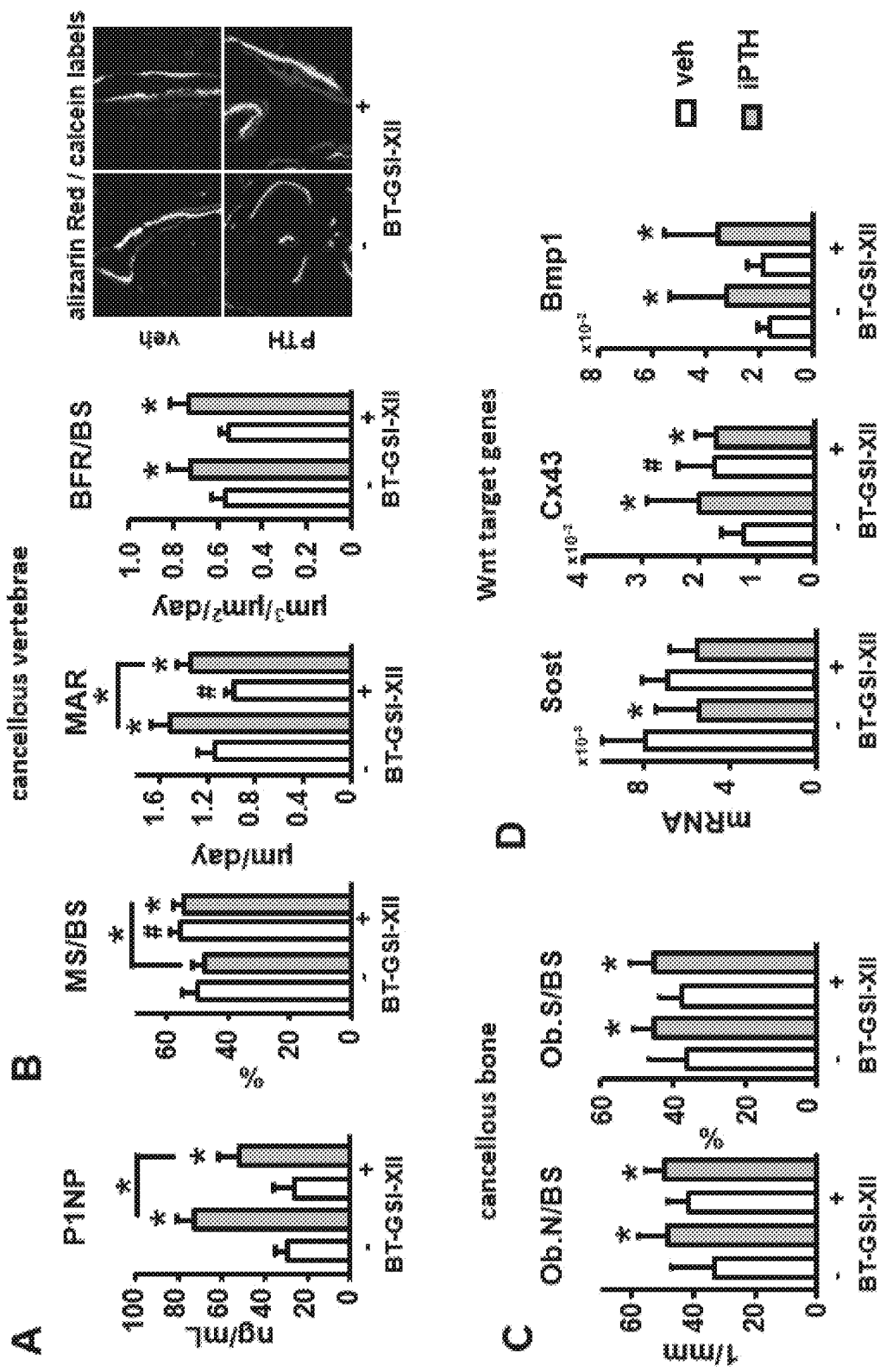
FIG. 13A-D

MATERIALS AND METHODS FOR SUPPRESSING AND/OR TREATING BONE RELATED DISEASES AND SYMPTOMS

CROSS-REFERENCE TO RELATED APPLICATIONS

The present application is a national stage entry of International (PCT) Patent Application No. PCT/US2018/045037, filed Aug. 2, 2018, which claims the benefit of U.S. Provisional Patent Application No. 62/540,396, filed Aug. 2, 2017, the disclosures of both of which are incorporated herein by reference in its entirety.

STATEMENT OF GOVERNMENTAL RIGHTS

This invention was made with government support under DK076007 and CA209882 awarded by National Institutes of Health and BX002104 merit award by the Veterans Administration. The government has certain rights in the invention.

FIELD OF THE INVENTION

Various aspects and embodiments disclosed herein relate generally to the modeling, treatment, reducing resistance to the treatment, prevention, and diagnosis of diseases/symptoms induced by multiple myeloma and/or other bone related diseases.

BACKGROUND

Multiple myeloma is a plasma cell malignancy characterized by expansion of monoclonal plasma cells in the bone marrow (BM) and the presence of osteolytic lesions. Multiple myeloma has one of the highest incidences of bone involvement among malignant diseases. It is estimated that up to 90% of patients with multiple myeloma have evidence of osteolysis in the form of generalized osteopenia or discrete lytic lesions, and up to 60% of multiple myeloma patients develop pathologic fractures. Multiple myeloma patients present with severe bone pain caused by osteolytic lesions that rarely heal. The osteolytic lesions are thought to result from increased bone resorption and concomitant long-term suppression of bone formation. The bone and BM microenvironment is a major contributor to tumor growth and bone destructive process in multiple myeloma.

Notch signaling mediates cell-to-cell communication among myeloma cells and other cells in the bone marrow favoring growth and survival of myeloma cells and increasing osteoclast formation. In vitro and in vivo studies demonstrated that systemic inhibition of Notch signaling using gamma-secretase inhibitors (GSIs) decreases the growth of myeloma cells and osteoclast differentiation. However, the use of GSIs in the clinic is limited by the presence of severe adverse side effects such as fatigue, skin disorders, and acute gastrointestinal toxicity. Therefore, development of a new class of drugs is much needed.

SUMMARY OF THE INVENTION

A first embodiment includes at least one compound of the formula A-Y—B, or a pharmaceutically acceptable salt thereof, or a metabolite thereof, wherein A is at least one agent that reduces and/or inhibits the activity of gamma-secretase; B is at least one bone-targeting molecule; and Y is a linker that joins and/or links A and B.

A second embodiment includes the compound according to the first embodiment, wherein A is the at least one agent that reduces and/or inhibits the activity of gamma-secretase; Y is the linker comprising the formula $NR_1$;

$R_1$ is $NR_2R_3$, $NR_2S(=O)_2R_3$ or $R_2OR_3$;

$R_2$ and $R_3$ are independently selected from H; $C_1$-$C_3$ alkyl, $C_1$-$C_4$ alkyl, $C_1$-$C_5$ alkyl, $C_1$-$C_6$ alkyl, $C_1$-$C_7$ alkyl, $C_1$-$C_5$ alkyl, $C_1$-$C_9$ alkyl, $C_1$-$C_{10}$ alkyl, $C_1$ alkyl, $C_2$ alkyl, $C_3$ alkyl, $C_4$ alkyl, $C_5$ alkyl, $C_5$ alkyl, $C_6$ alkyl, $C_7$ alkyl, $C_8$ alkyl, $C_9$ alkyl, $C_{10}$ alkyl, or any combination thereof; $C_1$-$C_3$ alkoxy, $C_1$-$C_4$ alkoxy, $C_1$-$C_5$ alkoxy, $C_1$-$C_6$ alkoxy, $C_1$-$C_7$ alkoxy, $C_1$-$C_5$ alkoxy, $C_1$-$C_9$ alkoxy, $C_1$-$C_{10}$ alkoxy, $C_1$ alkoxy, $C_2$ alkoxy, $C_3$ alkoxy, $C_4$ alkoxy, $C_5$ alkoxy, $C_5$ alkoxy, $C_6$ alkoxy, $C_7$ alkoxy, $C_8$ alkoxy, $C_9$ alkoxy 1, $C_{10}$ alkoxy, or any combination thereof; $C_6H_5OR_4$; benzoyl isoleucine; leucine aldehyde; phenyl optionally substituted with $C_1$-$C_{10}$ alkyl or any of the individual alkyl groups of formula $C_1$-$C_{10}$ alkyl, $C_1$-$C_{10}$ alkoxy or any of the individual alkoxy groups of formula $C_1$-$C_{10}$ alkoxy, carbonyl, or amide; or benzyl optionally substituted with $C_1$-$C_{10}$ alkyl or any of the individual alkyl groups of formula $C_1$-$C_{10}$ alkyl, $C_1$-$C_{10}$ alkoxy or any of the individual alkoxy groups of formula $C_1$-$C_{10}$ alkoxy, carbonyl, or amide;

$R_4$ is $C_1$-$C_{10}$ alkyl or any of the individual alkyl groups of formula $C_1$-$C_{10}$ alkyl, $C_1$-$C_{10}$ alkoxy or any of the individual alkoxy groups of formula $C_1$-$C_{10}$ alkoxy, carbonyl, or amide; and B is at least one biphosphonate optionally substituted with OH, halogen, $CH_3$, $NH_2$, N-alkyl, or N-dialkyl; or a pharmaceutically acceptable salt thereof, or a metabolite thereof.

A third embodiment includes the compound according to any one of the first and the second embodiments, wherein A is a gamma-secretase inhibitor comprising the formula:

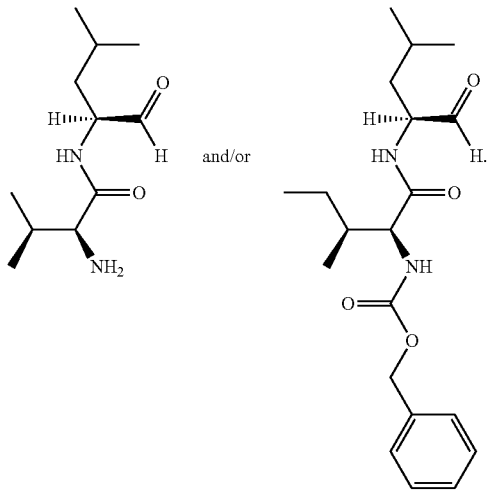

A fourth embodiment includes the compound according to any one of the first and the second embodiments, wherein the compound comprises one or more stereoisomers of the formula:

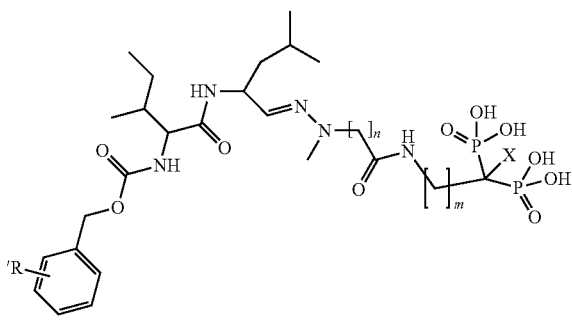

wherein 'R is H, CH$_3$, alkyl, halogen, CF$_3$, CN, OH, OCH$_3$, or O-alkyl;
n is 1, 2, 3, 4, 5, 6, 7, 8, or 9;
m is 0, 1, 2, 3, 4, 5, 6, 7, 8, or 9; and
X is H, OH, halogen, CH$_3$, NH$_2$, N-alkyl, or N-dialkyl; or a pharmaceutically acceptable salt thereof, or a metabolite thereof.

In some embodiments, the one or more stereoisomers according to the fourth embodiments, comprise any one or more of the formula:

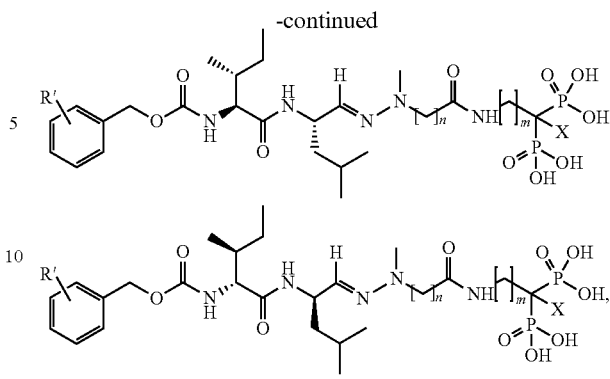

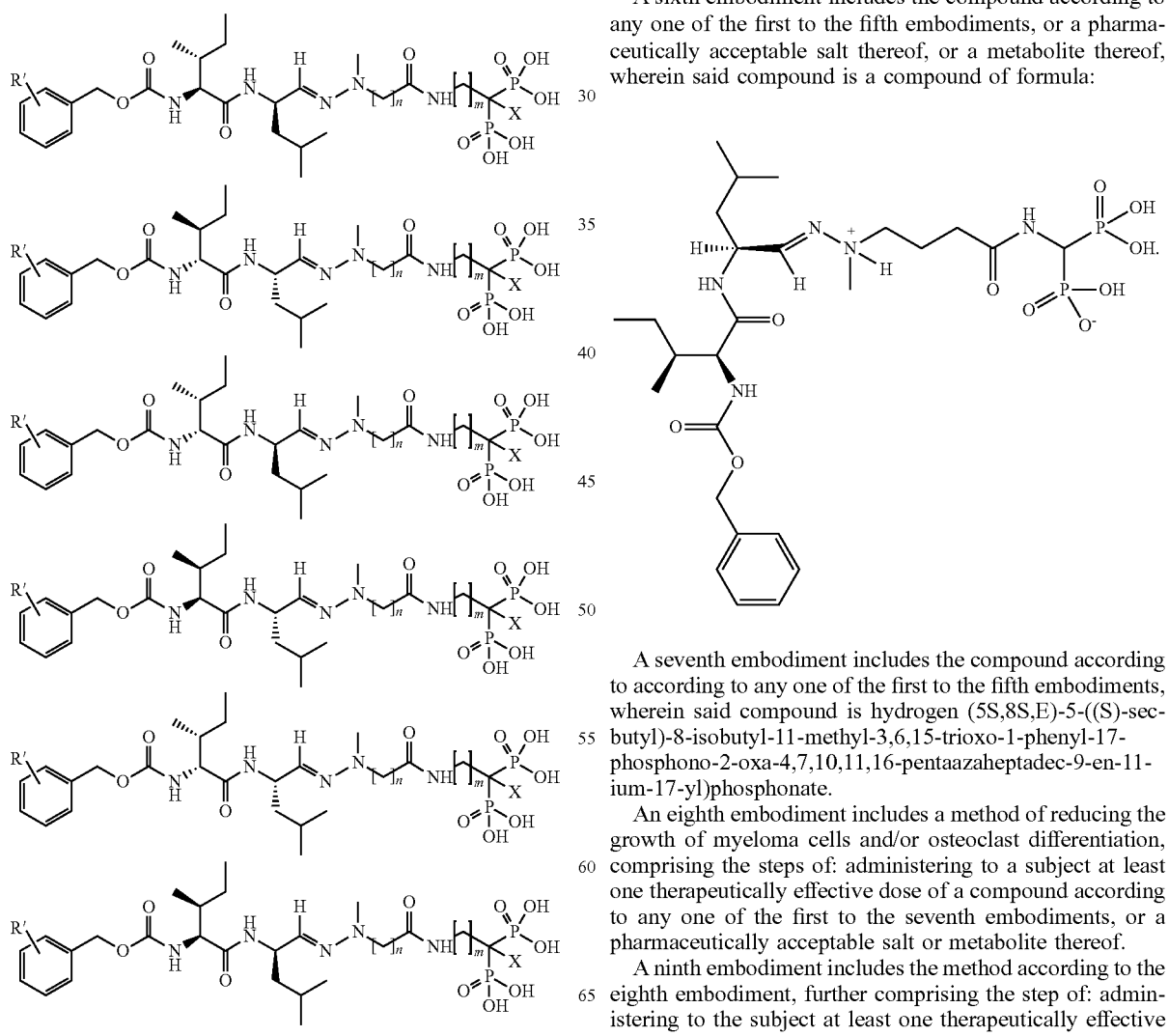

or a pharmaceutically acceptable salt thereof, or a metabolite thereof. Consistent with these embodiments, the one or more stereoisomers can include, but are not limited to, hydrogen (5S,8S,E)-5-((S)-sec-butyl)-8-isobutyl-11-methyl-3,6,15-trioxo-1-phenyl-17-phosphono-2-oxa-4,7,10,11,16-pentaazaheptadec-9-en-11-ium-17-yl)phosphonate.

A fifth embodiment includes the compound according to the fourth embodiment, wherein n is 1, 2, or 3, m is 0, and X is H.

A sixth embodiment includes the compound according to any one of the first to the fifth embodiments, or a pharmaceutically acceptable salt thereof, or a metabolite thereof, wherein said compound is a compound of formula:

A seventh embodiment includes the compound according to according to any one of the first to the fifth embodiments, wherein said compound is hydrogen (5S,8S,E)-5-((S)-sec-butyl)-8-isobutyl-11-methyl-3,6,15-trioxo-1-phenyl-17-phosphono-2-oxa-4,7,10,11,16-pentaazaheptadec-9-en-11-ium-17-yl)phosphonate.

An eighth embodiment includes a method of reducing the growth of myeloma cells and/or osteoclast differentiation, comprising the steps of: administering to a subject at least one therapeutically effective dose of a compound according to any one of the first to the seventh embodiments, or a pharmaceutically acceptable salt or metabolite thereof.

A ninth embodiment includes the method according to the eighth embodiment, further comprising the step of: administering to the subject at least one therapeutically effective dose of parathyroid hormone.

A tenth embodiment includes the method according to any one of the eighth and the ninth embodiments, further comprising the step of: administering to the subject at least one therapeutically effective dose of at least one proteasome inhibitor.

An eleventh embodiment includes the method according to the tenth embodiment, wherein the at least one proteasome inhibitor comprises lactacystin, disulfiram, epigallocatechin-3-gallate, marizomib (salinosporamide A), oprozomib (ONX-0912), delanzomib (CEP-18770), epoxomicin, beta-hydroxy beta-methylbutyrate, bortezomib, carfilzomib, and/or ixazomib.

A twelfth embodiment includes the method according to any one of the eighth to the eleventh embodiments, wherein the subject comprises a human, an animal, a cell, and/or a tissue.

A thirteenth embodiment includes a method of treating a bone related disease, comprising the steps of: administering to a subject at least one therapeutically effective dose of a compound according to any one of the first to the seventh embodiments, or a pharmaceutically acceptable salt or metabolite thereof.

A fourteenth embodiment includes the method according to the thirteenth embodiment, further comprising the step of: administering to the subject at least one therapeutically effective dose of parathyroid hormone.

A fifteenth embodiment includes the method according to any one of the thirteenth and the fourteenth embodiments, further comprising the step of: administering to the subject at least one therapeutically effective dose of at least one proteasome inhibitor.

A sixteenth embodiment includes the method according to the fifteenth embodiment, wherein the at least one proteasome inhibitor comprises lactacystin, disulfiram, epigallocatechin-3-gallate, marizomib (salinosporamide A), oprozomib (ONX-0912), delanzomib (CEP-18770), epoxomicin, beta-hydroxy beta-methylbutyrate, bortezomib, carfilzomib, and/or ixazomib.

A seventeenth embodiment includes the method according to any one of the thirteenth to the sixteenth embodiments, wherein the bone related disease comprises osteopenia, osteoporosis, rheumatoid arthritis, hematologic, gastrointestinal and pulmonary disease, autoimmunity, transplant rejection, multiple myeloma, bone cancer, brain cancer, breast cancer, endocrine cancer, gastrointestinal cancer, gynecologic cancer, prostate cancer, head and neck cancer, hematologic cancer, lung cancer, renal cell carcinoma, skin cancer, urologic cancer, rare cancer, skeletal or bone diseases, defects, and/or conditions associated with or induced by glucocorticoid therapy.

An eighteenth embodiment includes the method according to any one of claims the thirteenth to the seventeenth embodiments, wherein the subject comprises a human, an animal, a cell, and/or a tissue.

A nineteenth embodiment includes a method of treating a bone related disease, comprising the steps of: administering to a subject at least one therapeutically effective dose of at least one agent that reduces and/or inhibits the activity of gamma-secretase, or a pharmaceutically acceptable salt or metabolite thereof; and at least one biphosphonate, or a pharmaceutically acceptable salt or metabolite thereof.

A twentieth embodiment includes the method according to the nineteenth embodiment, further comprising the step of: administering to the subject at least one therapeutically effective dose of parathyroid hormone.

A twenty first embodiment includes the method according to any one of the nineteenth and the twentieth embodiments, further comprising the step of: administering to the subject at least one therapeutically effective dose of at least one proteasome inhibitor.

A twenty second embodiment includes the method according to the twenty first embodiment, wherein the at least one proteasome inhibitor comprises lactacystin, disulfiram, epigallocatechin-3-gallate, marizomib (salinosporamide A), oprozomib (ONX-0912), delanzomib (CEP-18770), epoxomicin, beta-hydroxy beta-methylbutyrate, bortezomib, carfilzomib, and/or ixazomib.

A twenty third embodiment includes the method according to any one of the nineteenth to the twenty second embodiments, wherein the at least one agent that reduces and/or inhibits the activitiy of gamma-secretase comprises a compound having the formula:

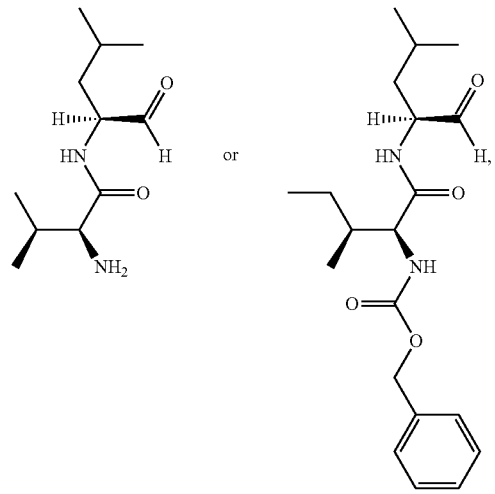

or a pharmaceutically acceptable salt thereof, or a metabolite thereof.

A twenty fourth embodiment includes the method according to any one of the nineteenth to the twenty third embodiments, wherein the bone related disease comprises osteopenia, osteoporosis, rheumatoid arthritis, hematologic, gastrointestinal and pulmonary disease, autoimmunity, transplant rejection, multiple myeloma, bone cancer, brain cancer, breast cancer, endocrine cancer, gastrointestinal cancer, gynecologic cancer, prostate cancer, head and neck cancer, hematologic cancer, lung cancer, renal cell carcinoma, skin cancer, urologic cancer, rare cancer, skeletal or bone diseases, defects, and/or conditions associated with or induced by glucocorticoid therapy.

A twenty fifth embodiment includes the method according to any one of the nineteenth to the twenty fourth embodiments, wherein the subject comprises a human, an animal, a cell, and/or a tissue.

A twenty sixth embodiment includes the method according to any one of the eighth to the twenty fifth embodiments, wherein the therapeutically effective dose of parathyroid hormone, is on the order of between about 0.01 µg to about 1000 µg and the dose of the compound is administered to the patient at least once per day. Consistent with these embodiments, the therapeutically effective dose of parathyroid hormone includes, but is not limited to, on the order of between: about 0.01 µg to about 1000 µg; about 0.01 µg to about 500 µg; about 0.01 µg to about 200 µg; about 0.01 µg to about 150 µg; about 0.01 µg to about 100 mg; about 0.01 µg to about 80 µg; about 0.01 µg to about 50 µg; about 0.05

μg to about 100 mg; about 0.05 μg to about 80 μg; about 0.05 μg to about 50 μg; about 0.1 μg to about 100 μg; about 0.1 μg to about 50 μg; about 0.2 μg to about 100 μg; about 0.2 μg to about 50 μg; about 0.5 μg to about 100 μg; about 0.5 μg to about 50 μg; about 10 μg to about 200 μg; about 50 μg to about 200 μg; about 10 μg to about 100 μg; about 50 μg to about 100 μg; about 100 μg to about 150 μg; about 10 μg, about 20 μg, about 30 μg, about 40 μg, about 50 μg, about 60 μg, about 70 μg, about 80 μg, about 90 μg, about 100 μg, and/or any combination thereof.

A twenty seventh embodiment includes the method according to any one of the eighth to the twenty sixth embodiments, wherein the therapeutically effective dose of a compound according to any one of the first to the seventh embodiments, or a pharmaceutically acceptable salt or metabolite thereof, is on the order of between about 0.001 μg to about 1000 μg and the dose of the compound is administered to the patient at least once per day. Consistent with these embodiments, the therapeutically effective dose of a compound according to any one of the first to the seventh embodiments, or a pharmaceutically acceptable salt or metabolite thereof, includes, but is not limited to, on the order of between: about 0.001 μg to about 1000 μg; about 0.001 μg to about 500 μg; about 0.001 μg to about 200 μg; about 0.001 μg to about 150 μg; about 0.001 μg to about 100 mg; about 0.001 μg to about 80 μg; about 0.001 μg to about 60 μg; about 0.005 μg to about 100 mg; about 0.005 μg to about 80 μg; about 0.005 μg to about 50 μg; about 0.01 μg to about 100 μg; about 0.01 μg to about 50 μg; about 0.02 μg to about 100 μg; about 0.02 μg to about 50 μg; about 0.05 μg to about 100 μg; about 0.05 μg to about 50 μg; about 1 μg to about 200 μg; about 1 μg to about 150 μg; about 1 μg to about 100 μg; about 1 μg to about 50 μg; about 0.01 μg, about 0.1 μg, about 1 μg, about 5 μg, about 10 μg, about 20 μg, about 30 μg, about 40 μg, about 50 μg, about 60 μg, about 70 μg, about 80 μg, about 90 μg, about 100 μg, and/or any combination thereof.

A twenty eighth embodiment includes the method according to any one of the eighth to the twenty sixth embodiments, wherein the compound according to any one of the first to the seventh embodiments, or a pharmaceutically acceptable salt or metabolite thereof is formulated for administration to the subject for delivery orally, subcutaneously, intramuscularly, intradermally, intranasally, topically, transdermally, parenterally, gastrointestinally, transbronchially, transalveolarly, and/or mucosally.

A twenty ninth embodiment includes the method according to any one of the eighth to the twenty eighth embodiments, wherein parathyroid hormone and/or the at least one proteasome inhibitor is formulated for administration to the subject for delivery orally, subcutaneously, intramuscularly, intradermally, intranasally, topically, transdermally, parenterally, gastrointestinally, transbronchially, transalveolarly, and/or mucosally.

A thirtieth embodiment includes a composition comprising the compound according to any one of the first to the seventh embodiments, or a pharmaceutically acceptable salt or metabolite thereof and at least one agent that induces bone anabolism.

A thirty first embodiment includes the composition according to the thirtieth embodiment, wherein the at least one agent that induces bone anabolism includes, but is not limited to, parathyroid hormone.

A thirty second embodiment includes the composition according to the thirtieth and the thirty first embodiments, wherein the composition increases bone mass in a subject.

A thirty third embodiment includes the composition according to any one of the thirtieth and the thirty second embodiments, wherein the compound according to any one of the first to the seventh embodiments and parathyroid hormone are present in the composition in a concentration ratio such that the composition exhibits synergy. Consistent with these embodiments, the concentration ratio of the compound according to any one of the first to the seventh embodiments and parathyroid hormone can be from about 100:1 to about 1:100, from about 90:1 to about 1:90, from about 80:1 to 1:80, from about 50:1 to about 1:50, from about 20:1 to about 1:20, from about 10:1 to about 1:10, from about 8:1 to 1:8, from about 5:1 to about 1:5, from about 2:1 to about 1:2, from about 1:1 to about 1:1, about 100:1, about 50:1, about 20:1, about 10:1, about 5:1, about 2:1, about 1:1, about 1:2, about 1:5, about 1:10, about 1:20, about 1:50, about 1:100, or any combination thereof.

A thirty fourth embodiment includes the composition according to any one of the thirtieth to the thirty third embodiments, further comprising at least one proteasome inhibitor.

A thirty fifth embodiment includes the composition according to the thirty fourth embodiments, wherein the at least one proteasome inhibitor comprises lactacystin, disulfiram, epigallocatechin-3-gallate, marizomib (salinosporamide A), oprozomib (ONX-0912), delanzomib (CEP-18770), epoxomicin, beta-hydroxy beta-methylbutyrate, bortezomib, carfilzomib, and/or ixazomib.

A thirty sixth embodiment includes the composition according to any one of the thirtieth to the thirty fifth embodiments, wherein the subject comprises a human, an animal, a cell, and/or a tissue.

BRIEF DESCRIPTION OF THE FIGURES

FIG. 3A. Graphs illustrating the effect on pro- and anti-osteoclastogenic cytokines. Mice treated with BT-GSI-XII exhibit increased Opg mRNA expression in bone, thus decreasing the Rankl/Opg ratio.

FIG. 3B. Graphs illustrating the effect on osteoblast markers. The expression of osteoblast markers remained unchanged by BT-GSI-XII.

FIG. 4. Exemplary structural formula of some of UR-15 (also referred to as BT-GSI-XII) analogs.

FIG. 12A. A graph illustrating the effect of daily injections of PTH (iPTH) and BT-GSI-XII on the serum levels of the bone resorption marker C-terminal telopeptide (CTX).

FIG. 12B. (Left) Graphs illustrating the effect of daily injections of PTH (iPTH) and BT-GSI-XII on the level of osteoclast number per bone surface (Oc.N/BS) and osteoclast surface per bone surface (Oc.S/BS) in cancellous bone. (Right) Representative TRAP staining illustrating the effect of daily injections of PTH (iPTH) and BT-GSI-XII on osteocalsts in cancellous bone.

FIG. 12C. Graphs illustrating the effect of daily injections of PTH (iPTH) and BT-GSI-XII on the mRNA gene expression of pro- and anti-osteoclastogenic cytokines.

FIG. 12D. A graph illustrating the effect of BT-GSI-XII on the number of osteoclast.

FIG. 13A. A graph illustrating the effect of daily injections of PTH (iPTH) and BT-GSI-XII on the serum levels of the bone formation marker procollagen type 1 amino-terminal propeptide (P1NP).

FIG. 13B. (Left) Graphs illustrating the effect of daily injections of PTH (iPTH) and BT-GSI-XII on the level of mineralizing surface per bone surface (MS/BS), mineral apposition rate (MAR), bone formation rate per unit of bone surface (BFR/BS). (Right) Representative alizarin Red/calcein labels staining illustrating the effect of daily injections of PTH (iPTH) and BT-GSI-XII on cancellous vertebrae.

FIG. 13C. Graphs illustrating the effect of daily injections of PTH (iPTH) and BT-GSI-XII on the level of osteoblast number per bone surface (Ob.N/BS) and osteoblast surface per bone surface (Ob.S/BS) in cancellous bone.

FIG. 13D. Graphs illustrating the effect of daily injections of PTH (iPTH) and BT-GSI-XII on the level of Wnt target gene expression.

DESCRIPTION

Figure 1:
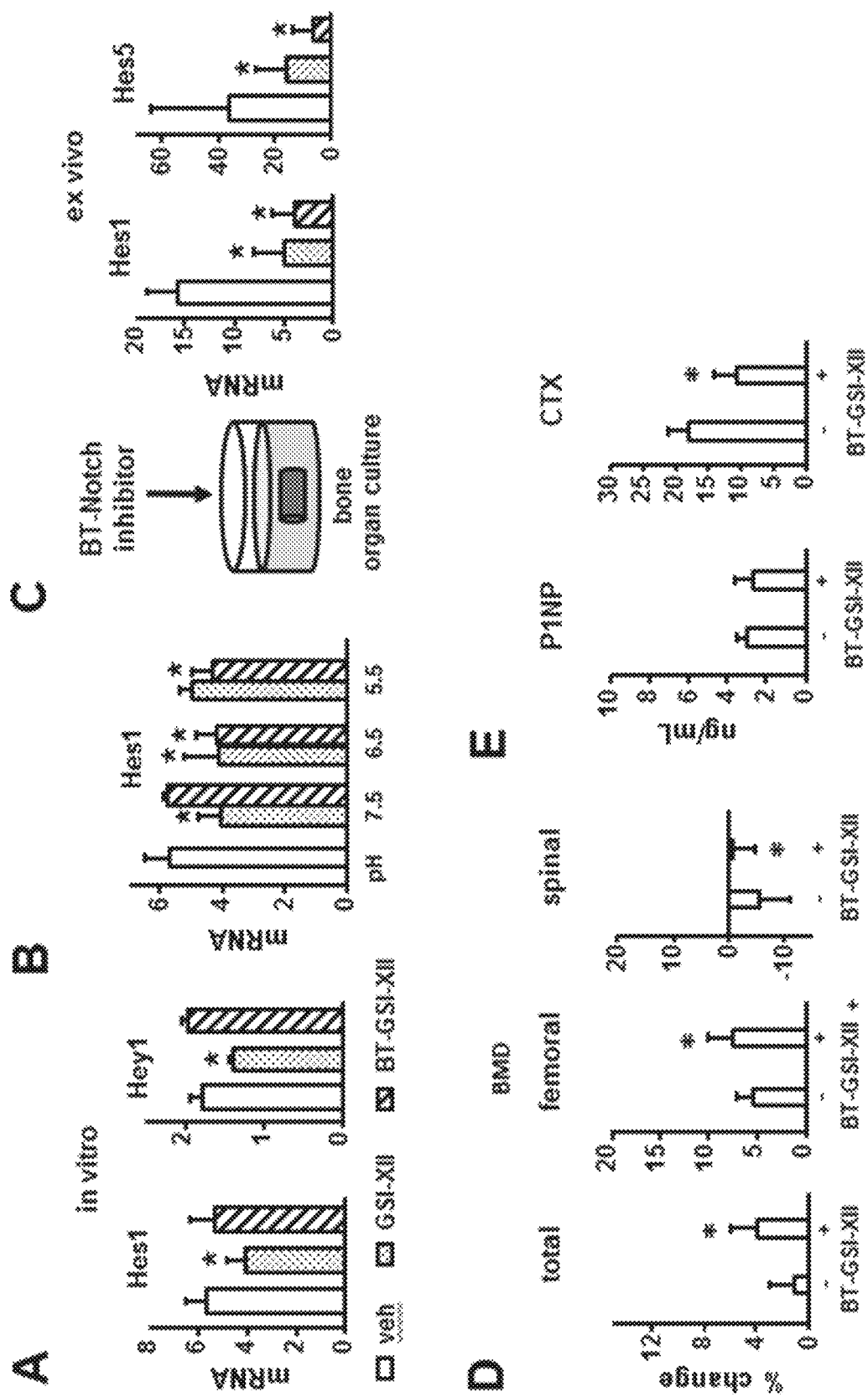
FIG. 1A. Graphs illustrating the effect on Notch target gene expression. In vitro, the control unconjugated GSI decreased Notch target gene expression (Hes1-Hey1) but BT-GSI-XII had no effect.
FIG. 1B. A graph illustrating the effect on Notch target gene expression. GSI-XII and BT-GSI-XII preincubated at low pH to mimic the acidic conditions in resorption sites exhibit equal inhibition of Notch target gene expression.
FIG. 1C. A schematic drawing illustrating an exemplary ex vivo system. Ex vivo, both GSI-XII and BT-GSI-XII (non-preincubated) similarly decreased Hes1/5 expression in whole bone organ cultures that reproduce conditions in the bone microenvironment.
FIG. 1D. Graphs illustrating the effect of BT-GSI-XII on Bone Mineral Density (BMD). BT-GSI-XII treated mice exhibited higher total (3%), femoral (4%), and spinal (7%) BMD compared to control mice.
FIG. 1E. Graphs illustrating the effect of BT-GSI-XII on the bone formation markers. BT-GSI-XII did not affect the circulating levels of the bone formation marker P1NP, but decreased serum CTX by 40%, a marker of bone resorption.

For the purposes of promoting an understanding of the principles of the novel technology, reference will now be made to the preferred embodiments thereof, and specific language will be used to describe the same. It will nevertheless be understood that no limitation of the scope of the novel technology is thereby intended, such alterations, modifications, and further applications of the principles of the novel technology being contemplated as would normally occur to one skilled in the art to which the novel technology relates are within the scope of this disclosure and the claims.

As used herein, unless explicitly stated otherwise or clearly implied otherwise the term 'about' refers to a range of values plus or minus 10 percent, e.g. about 1.0 encompasses values from 0.9 to 1.1.

The term, "treating" as used herein unless stated or implied otherwise, includes administering to a human or an animal patient at least one dose of a compound, treating includes preventing or lessening the likelihood and/or severity of at least one disease as well as limiting the length of an illness or the severity of an illness, treating may or may not result in a cure of the disease.

As used herein, unless explicitly stated otherwise or clearly implied otherwise the terms 'therapeutically effective dose,' 'therapeutically effective amounts,' and the like, refer to a portion of a compound that has a net positive effect on health and well being of a human or other animal. Therapeutic effects may include an improvement in longevity, quality of life and the like these effects also may also include a reduced susceptibility to developing disease or deteriorating health or well being. The effects may be immediate realized after a single dose and/or treatment or they may be cumulative realized after a series of doses and/or treatments. A "therapeutically effective amount" in general means the amount that, when administered to a subject or animal for treating a disease, is sufficient to affect the desired degree of treatment for the disease.

As used herein, "inhibition" or "inhibitory activity" each encompass whole or partial reduction of activity or effect of an enzyme or all and/or part of a pathway that includes an enzyme that is effected either directly or indirectly by the inhibitor or a pathway that is effected either directly or indirectly by the activity of the enzyme which is effected either directly or indirectly by the inhibitor.

As used herein, the term "pharmaceutically acceptable salt" is defined as a salt wherein the desired biological activity of the inhibitor is maintained and which exhibits a minimum of undesired toxicological effects. Non-limiting examples of such a salt are (a) acid addition salts formed with inorganic acids (e.g., hydrochloric acid, hydrobromic acid, sulphuric acid, phosphoric acid, nitric acid, and the like), and salts formed with organic acids (such as e.g. acetic acid, oxalic acid, tartaric acid, succinic acid, malic acid, ascorbic acid, benzoic acid, tannic acid, palmitic acid, polyglutamic acid, naphthalene sulphonic acid, naphthalene disulphonic acid, polygalacturonic acid and the like); (b) base additional salts formed with metal cations such as zinc, calcium, bismuth, barium, magnesium, aluminum, copper, cobalt, nickel, cadmium, sodium, potassium and the like, or with a cation formed from ammonia, N,N-dibenzylethylenediamine, D-glucosamine, tetraethylammonium or ethylenediamine; or (c) combinations of (a) and (b); e.g. a zinc tannate or the like.

Pharmaceutically acceptable salts include salts of compounds of the invention that are safe and effective for use in mammals and that possess a desired therapeutic activity. Pharmaceutically acceptable salts include salts of acidic or basic groups present in compounds of the invention. Pharmaceutically acceptable acid addition salts include, but are not limited to, hydrochloride, hydrobromide, hydroiodide, nitrate, sulfate, bisulfate, phosphate, acid phosphate, isonicotinate, acetate, lactate, salicylate, citrate, tartrate, pantothenate, bitartrate, ascorbate, succinate, maleate, gentisinate, fumarate, gluconate, glucaronate, saccharate, formate, benzoate, glutamate, methanesulfonate, ethanesulfonate, benzensulfonate, p-toluenesulfonate and pamoate (i.e., 1,1'-methylene-bis-(2-hydroxy-3-naphthoate)) salts. Certain compounds of the invention may form pharmaceutically acceptable salts with various amino acids. Suitable base salts include, but are not limited to, aluminum, calcium, lithium, magnesium, potassium, sodium, zinc, and diethanolamine salts. For additional information on some pharmaceutically acceptable salts that can be used to practice the invention please reviews such as Berge, et al., 66 J. PHARM. SCI. 1-19 (1977), Haynes, et al, J. Pharma. Sci., Vol. 94, No. 10, October 2005, pgs. 2111-2120 and See, e.g., P. Stahl, et al., HANDBOOK OF PHARMACEUTICAL SALTS: PROPERTIES, SELECTION AND USE, (VCHA/Wiley-VCH, 2002); S. M. Berge, et al., "Pharmaceutical Salts," *Journal of Pharmaceutical Sciences*, Vol. 66, No. 1, January 1977.

Pharmaceutical formulation: The compounds of the invention and their salts may be formulated as pharmaceutical compositions for administration. Such pharmaceutical compositions and processes for making the same are known in the art for both humans and non-human mammals. See, e.g., REMINGTON: THE SCIENCE AND PRACTICE OF PHARMACY, (A. Gennaro, et al., eds., 19$^{th}$ ed., Mack Publishing Co., 1995). Formulations can be administered through various means, including oral administration, parenteral administration such as injection (intramuscular, subcutaneous, intravenous, intraperitoneal) or the like; transdermal administration such as dipping, spray, bathing, washing, pouring-on and spotting-on, and dusting, or the like. Additional active ingredients may be included in the formulation containing a compound of the invention or a salt thereof.

The pharmaceutical formulations of the present invention include those suitable for oral, parenteral (including subcutaneous, intradermal, intramuscular and intravenous) and rectal administration. The formulations may be presented in unit dosage form and may be prepared by any of the methods well known in the art of pharmacy. All methods include the step of bringing into association the active ingredient, i.e., the compound or salt of the present invention, with the carrier. In general, the formulations are prepared by uniformly and intimately bringing into association the active ingredient with a liquid carrier or, a finely divided solid carrier or both, and then, if necessary, forming the associated mixture into the desired formulation.

The pharmaceutical formulations of the present invention suitable for oral administration may be presented as discrete units, such as a capsule, cachet, tablet, or lozenge, each containing a predetermined amount of the active ingredient; as a powder or granules; as a solution or a suspension in an aqueous liquid or non-aqueous liquid such as a syrup, elixir or a draught, or as an oil-in-water liquid emulsion or a water-in-oil liquid emulsion. The formulation may also be a bolus, electuary or paste.

The pharmaceutical formulations of the present invention suitable for parenteral administration include aqueous and non-aqueous sterile injection solutions, and may also include an antioxidant, buffer, a bacteriostat and a solution which renders the composition isotonic with the blood of the recipient, and aqueous and non-aqueous sterile suspensions which may contain, for example, a suspending agent and a thickening agent. The formulations may be presented in a single unit-dose or multi-dose containers, and may be stored in a lyophilized condition requiring the addition of a sterile liquid carrier prior to use.

Pharmaceutically acceptable carrier: Pharmaceutically acceptable carrier, unless stated or implied otherwise, is used herein to describe any ingredient other than the active component(s) that may be included in a formulation. The choice of carrier will to a large extent depend on factors such as the particular mode of administration, the effect of the carrier on solubility and stability, and the nature of the dosage form.

A tablet may be made by compressing or moulding the active ingredient with the pharmaceutically acceptable carrier. Compressed tablets may be prepared by compressing in a suitable machine the active ingredient in a free-flowing form, such as a powder or granules, in admixture with, for example, a binding agent, an inert diluent, a lubricating agent, a disintegrating and/or a surface active agent. Moulded tablets may be prepared by moulding in a suitable machine a mixture of the powdered active ingredient moistened with an inert liquid diluent. The tablets may optionally be coated or scored and may be formulated so as to provide slow or controlled release of the active ingredient.

The term, "synergism" or "synergy" refers to an interaction of two or more factors such that the effect when combined is greater than the predicted effect based on the response of each factor applied separately.

As used herein, "bone related diseases" include, but are not limited to, osteopenia, osteoporosis, rheumatoid arthritis, hematologic, gastrointestinal and pulmonary diseases, autoimmunity, transplant rejection, multiple myeloma, bone cancer, brain cancer, breast cancer, endocrine cancer, gastrointestinal cancer, gynecologic cancer, prostate cancer, head and neck cancer, hematologic cancer, lung cancer, renal cell carcinoma, skin cancer, urologic cancer, rare cancers, and/or skeletal or bone diseases, defects, and/or conditions associated with or induced by glucocorticoid therapy.

As used herein, "proteasome inhibitors" include, but are not limited to, lactacystin, disulfiram, epigallocatechin-3-gallate, marizomib (salinosporamide A), oprozomib (ONX-0912), delanzomib (CEP-18770), epoxomicin, beta-hydroxy beta-methylbutyrate, bortezomib, carfilzomib, and ixazomib.

Multiple myeloma is a plasma cell malignancy characterized by expansion of monoclonal plasma cells in the bone marrow (BM) and the presence of osteolytic lesions. Multiple myeloma has the highest incidence of bone involvement among malignant diseases. Multiple myeloma patients present with severe bone pain caused by osteolytic lesions that rarely heal. The osteolytic lesions result from increased bone resorption and concomitant long-term suppression of bone formation. The bone and BM microenvironment is a major contributor to tumor growth and bone destructive process in multiple myeloma. See e.g., Jesus Delgado-Calle et. al., *Role of osteocytes in multiple myeloma bone disease*, CURR OPIN SUPPORT PALLIAT CARE, 2014; 8(4): 407-413.

Notch signaling plays a critical role in cell-to-cell communication among bone and bone marrow cells under physiological conditions and it favors growth and survival of cancer cells in bone. However, genetic manipulation of this pathway rendered different bone phenotypes depending on the Notch component (ligands, receptors, target genes), the cell lineage, or differentiation stage being targeted; and skeletal phenotypes result from combined developmental and postnatal effects. In vitro and in vivo studies demonstrated that systemic inhibition of Notch signaling using gamma-secretase inhibitors (GSIs) decreases the growth of myeloma cells and osteoclast differentiation. However, the use of GSIs in the clinic is limited by the presence of severe adverse side effects as fatigue, skin disorders, and acute gastrointestinal toxicity.

Bone fragility leading to fractures and disability is associated with the bone disease caused by glucocorticoid excess, sex steroid deficiency, and advanced age. Increased osteoblast apoptosis is at least partially responsible for the decreased bone formation rate associated with the osteopenia induced by glucocorticoid excess. Studies using osteocytic MLO-Y4 cells and primary murine calvaria cells demonstrated that bisphosphonates can inhibit apoptosis induced by the glucocorticoid dexamethasone, the inhibitor of DNA repair etoposide that blocks topo-isomerase II activity, or TNFα, an activator of death receptors. Bisphosphonates can stop bone loss by inhibiting the activity or by increasing the rate of apoptosis of bone resorbing osteoclasts. See e.g., Teresita Bellido et. al., *Novel actions of bisphosphonates in bone: Preservation of osteoblast and osteocyte viability*, BONE, 2011; 49(1): 50-55.

Sclerostin, the product of the Sost gene, is expressed and secreted primarily by osteocytes and inhibits bone formation by osteoblasts, fueled research attempting to identify regulators of this gene as well as other osteocyte products that impact the function of osteoblasts and osteoclasts. Parathyroid hormone (PTH), a central regulator of bone homeostasis, can inhibit sclerostin expression. See e.g., Teresita Bellido et. al., *Effects of PTH on osteocyte function*, BONE, 2013; 54(2): 250-257.

Synthesis Procedure

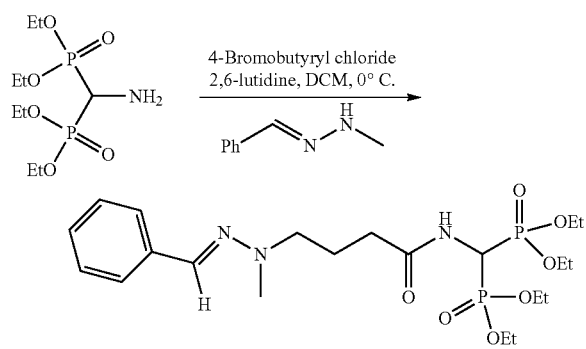

Tetraethyl (E) [4-(2-benzylidene-1-methylhydrazinyl)-butanamidomethylene]bisphosphonate A 10 mL round bottom flask was charged with dry DCM (1 mL), bisphosphonate amine (100 mg, 0.33 mmol, 1 equiv), and 2,6-lutidine (70.6 mg, 0.66 mmol, 2 equiv) at 0° C. under and Ar atmosphere. 4-bromobutyryl chloride (72 mg, 0.38 mmol, 1.2 equiv) was added into the reaction mixture. After stirring for 5 min, benzaldehyde N-methylhydrazone (133 mg, 0.99 mmol, 3 equiv) was added, and the reaction mixture was allowed to warm to rt and stir for 15 hr. The crude was purified directly by column chromatography with silica gel using ethyl acetate to elute the fore-running impurities then using acetone-ethyl acetate gradient (1:4 to 1:3) to afford the product (117 mg, 70%) as pale yellow oil.

$R_f$=0.43 (Ethyl Acetate-Acetone, 3:1). 12 active. $^1$H NMR (400 MHz, CDCl$_3$): δ 7.52 (d, J=7.6 Hz, 1H), 7.32-7.11 (m, 3H), 6.37 (s, 1H), 5.06 (td, J=21.8, 10.0 Hz, 1H), 4.17 (d, J=3.2 Hz, 8H), 3.65-3.26 (m, 2H), 2.88 (s, 3H), 2.45-2.37 (dd, J=29.1, 22.0 Hz, 2H), 2.14-2.01 (dd, J=30.3, 23.3 Hz, 2H), 1.31 (t, J=8.5 Hz, 12H). $^{13}$C NMR (101 MHz, CDCl$_3$): δ 171.81, 136.91, 131.66, 128.40, 127.11, 125.42, 63.55, 63.42, 57.30, 43.34, 37.55, 33.32, 32.72, 23.52, 16.29. $^{31}$P NMR (162 MHz, CDCl$_3$) δ 16.49, 13.24, 13.08. IR (cm$^{-1}$): 3248.13, 2981.95, 2908.65, 1674.21, 1529.55. LC-MS (APCI) m/z Calcd for C$_{21}$H$_{37}$N$_3$O$_7$P$_2$ (M+H$^+$): 505.21. Found: 505.87.

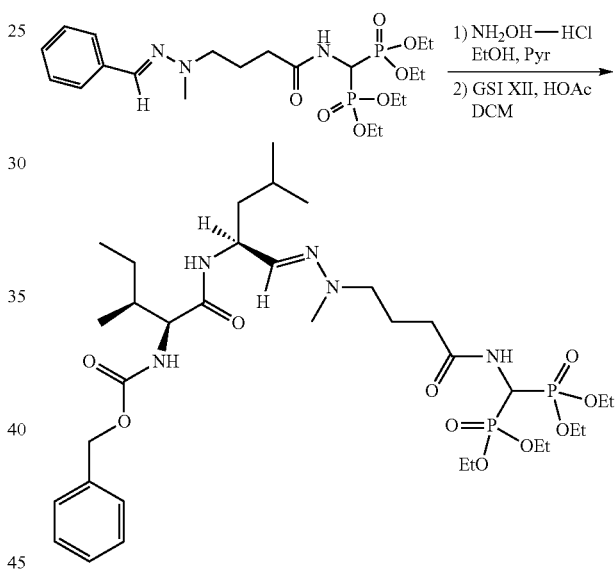

Benzyl (2S,3S)-1-[(S,E)-1-[2-(4-(bis-diethoxyphosphorylmethylene)amino)-4-oxobutyl)-2-methylhydrazinylidene)-4-methylpentan-2-yl)amino)-3-methyl-1-oxopentan-2-yl) carbamate A 10 mL round bottom flask was charged with tetraethyl (E) [4-(2-benzylidene-1-methylhydrazinyl)-butanamidomethylene] bisphosphonate (115 mg, 0.227 mmol, 1 equiv), pyridine (72 mg, 0.91 mmol, 4 equiv) in ethanol (1.5 mL). Hydroxylamine hydrochloride (63.2 mg, 0.91 mmol, 4 equiv) was added and the reaction mixture was then warmed to 70° C. for 14 hr. After cooling to rt, the reaction mixture was quenched with saturated NaHCO$_3$ (0.5 mL), and then basified with 1M NaOH solution. The reaction mixture was extracted with ethyl acetate (15 mL) for twice, and the aqueous layer was concentrated under vacuum to obtain white solid. Washed the solid with DCM then concentrated to obtain colorless oil (82 mg). Without further purification, the colorless oil was added into the solution of GSI XII (82 mg, 0.227 mmol, 1 equiv) in DCM (1.5 mL) with acetic acid (2.9 mg, 0.045 mmol, 0.2 equiv). The reaction mixture was allowed to reflux at 45° C. over-night for 12 hr. After cooling to rt, the crude was purified directly by column chromatography with silica gel using ethyl acetate to remove the easily eluted impurities then using methanol-ethyl acetate gradient (1:9) to afford the product (37 mg, 28%) as pale yellow oil.

$R_f$=0.32 (Acetate-Methanol, 9:1). CAM active. $^1$H NMR (400 MHz, CDCl$_3$): δ 7.68 (d, J=12.0 Hz, 1H), 7.49 (d, J=24.7 Hz, 1H), 7.33 (m, 5H), 6.83 (s, 1H), 6.59 (s, 1H), 5.11 (s, 2H), 4.56 (s, 1H), 4.20 (s, 8H), 4.10-3.95 (m, 1H), 3.15 (s, 1H), 2.68 (s, 3H), 2.29 (s, 2H), 1.89 (d, J=6.1 Hz, 3H), 1.67 (d, J=7.1 Hz, 2H), 1.49 (s, 4H), 1.47-1.25 (m, 12H), 1.09-0.78 (m, 12H). $^{13}$C NMR (101 MHz, CDCl$_3$): δ 172.97, 172.32, 171.06, 170.94, 170.61, 156.91, 156.36, 136.47, 134.01, 133.62, 128.38, 127.94, 127.81, 127.29, 66.55, 64.39, 63.36, 61.98, 59.80, 58.07, 56.67, 56.55, 49.74, (t, $J_{P\text{-}C}$=59.1 Hz), 44.65, 44.44, 43.18, 42.90, 42.73, 41.72, 38.67, 37.43, 37.26, 36.57, 34.11, 33.21, 24.77, 24.72, 24.60, 23.27, 23.02, 22.83, 22.67, 22.56, 22.23, 16.25, 15.49, 11.48, 11.27. $^{31}$P NMR (162 MHz, CDCl$_3$) δ 13.21. IR (cm$^{-1}$): 3271.33, 2960.78, 1704.14, 1656.88, 1530.54. LC-MS (APCI) m/z Calcd for C$_{34}$H$_{62}$N$_5$O$_{10}$P$_2$ (M+H$^+$): 762.39. Found: 762.20.

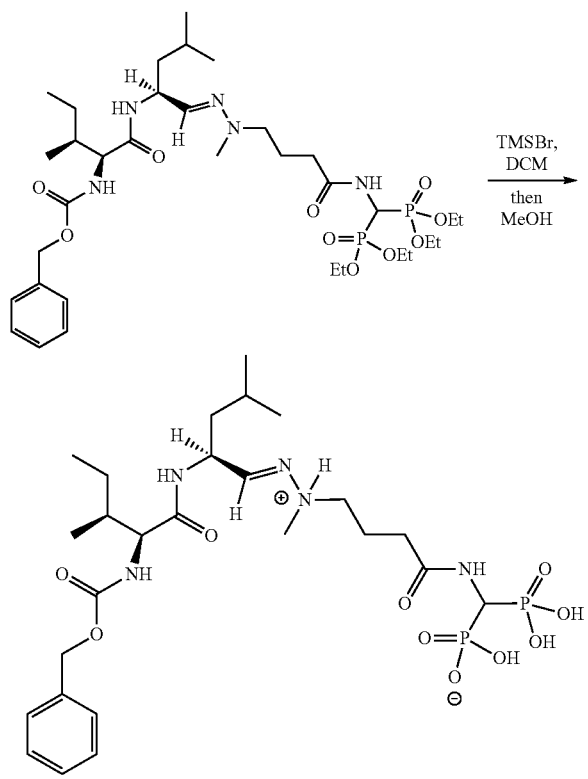

Hydrogen (5S,8S,E)-5-((S)-sec-butyl)-8-isobutyl-11-methyl-3,6,15-trioxo-1-phenyl-17-phosphono-2-oxa-4,7,10,11,16-pentaazaheptadec-9-en-11-ium-17-yl) phosphonate A dry 10 mL round bottom flask was charged with a solution of the foregoing hydrazone (1 eq, 0.046 mmol, 32 mg) in dry DCM (0.4 mL) under Ar at 0° C. Trimethylsilyl bromide (TMSBr) (6 eq, 0.28 mmol, 42.2 mg) was added dropwise with magnetic stirring. After addition was complete, the reaction mixture was allowed to stir and warm to rt overnight. The reaction mixture was then concentrated in vacuum and kept under high vacuum for 10 min to afford a brown solid. And methanol (3 mL) was added to dissolve the solid, and the resulting solution was concentrated in vacuum. This procedure was repeated 3 additional times. The solid was dried under high vacuum affording 28.7 mg of desired product as a pale yellow solid (99%).

$^1$H NMR (500 MHz, MeOD): δ 7.66-7.56 (m, 1H), 7.52 (s, 1H), 7.31 (m, 4H), 5.45 (s, 2H), 5.05 (s, 1H), 4.52 (s, 1H), 4.11 (s, 1H), 3.66-3.52 (m, 1H), 3.18 (d, J=6.9 Hz, 1H), 3.02 (s, 2H), 2.66 (s, 3H), 2.45 (s, 2H), 2.30 (s, 1H), 1.95 (s, 2H), 1.27 (t, J=11.4 Hz, 4H), 1.14-0.67 (m, 12H). $^{13}$C NMR (101 MHz, CDCl$_3$): δ 172.97, 172.32, 171.06, 170.94, 170.61, 156.91, 156.36, 136.47, 134.01, 133.62, 128.38, 127.94, 127.81, 127.29, 66.55, 64.39, 63.36, 61.98, 59.80, 58.07, 56.67, 56.55, 49.19 (t, J=59.1 Hz), 44.65, 44.44, 43.18, 42.90, 42.73, 41.72, 38.67, 37.43, 37.26, 36.57, 34.11, 33.21, 24.77, 24.72, 24.60, 23.27, 23.02, 22.83, 22.67, 22.56, 22.23, 16.25, 15.49, 11.48, 11.27. $^{31}$P NMR (162 MHz, CDCl$_3$) δ 15.44. IR (cm$^{-1}$): 3201.83, 3026.31, 2960.73, 2931.80, 2875.86, 2360.87, 1668.43, 1537.27. Thermo-MS (ESI) m/z: Calcd for C$_{27}$H$_{53}$N$_5$O$_{11}$P$_2$ (M+MeOH+4H$^+$): 685.32. Found: 685.40.

Examples

To at least reduce or circumvent the side effects associated with pan inhibition of Notch signaling using GSIs, novel Notch inhibitors were synthesized by linking, for example, GSI-XII to an inactive bone-targeting molecule (BT). The BT portion of the conjugate is though to direct the conjugate to bone where the linker is cleaved near osteoclasts, thus releasing GSI. Forms of BT useful for the application can include, but are not limited to, biphosphonates optionally substituted with OH, halogen, CH$_3$, NH$_2$, N-alkyl, or N-dialkyl. See, for example, FIGS. 4-8. BT-GSI was designed to direct the conjugate to bone where the linker is cleaved by, for example, acid produced by osteoclasts, thereby releasing GSI.

As used herein, unless explicitly stated otherwise or clearly implied otherwise the compound "BT-GSI-XII" comprises the formula:

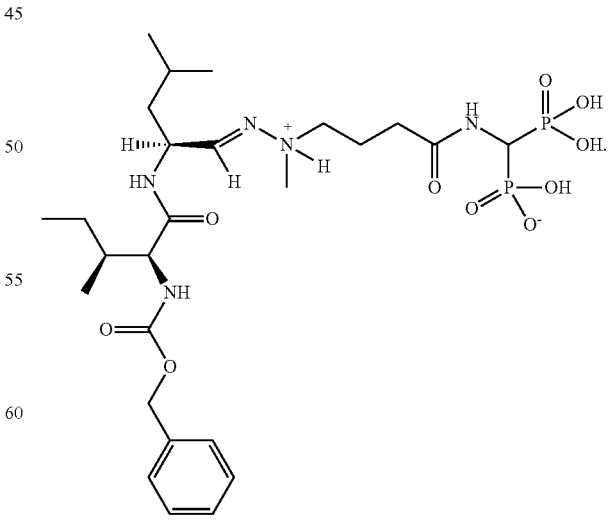

Figure 2A:
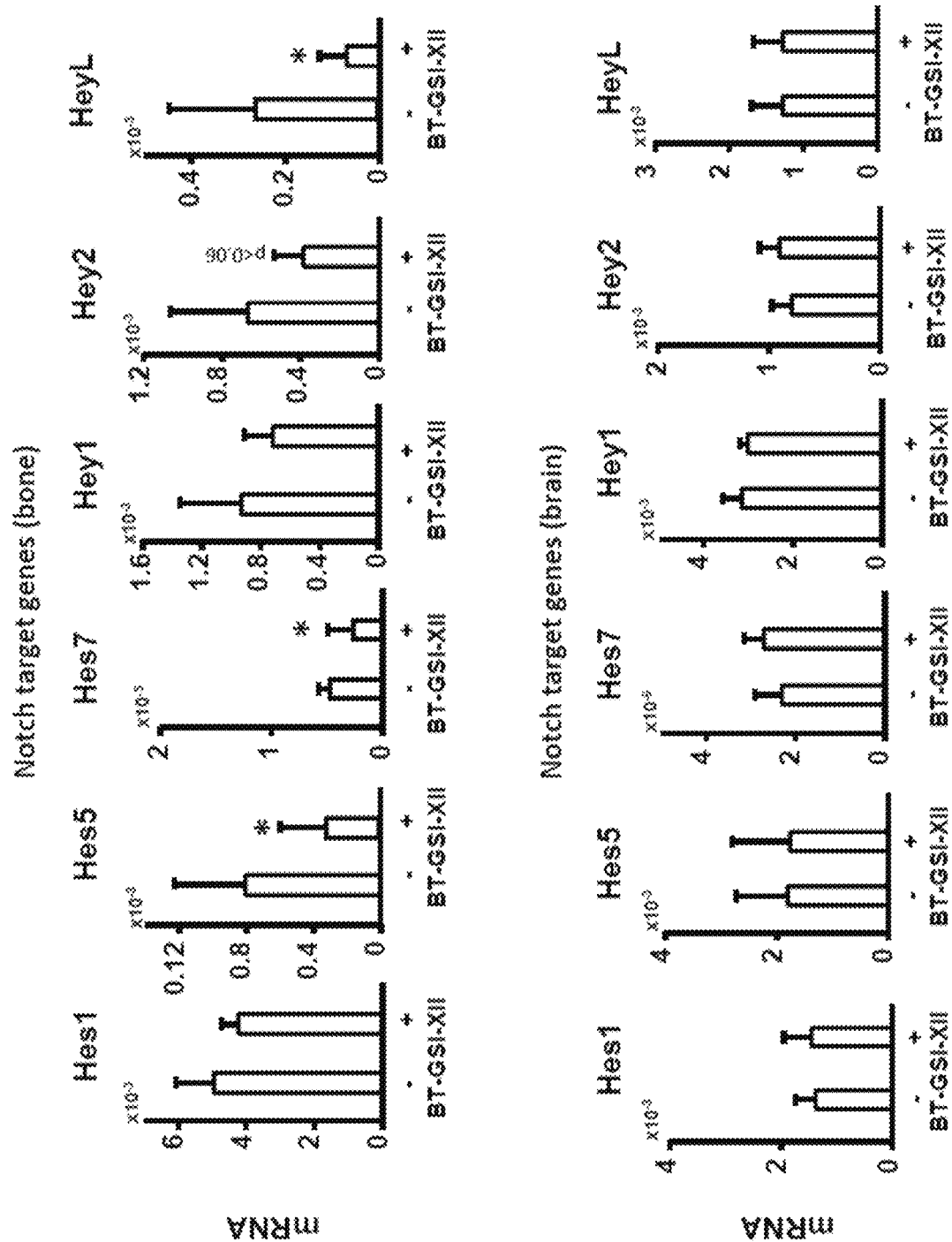
FIG. 2A. Graphs illustrating the effect on Notch target genes. Mice treated with BT-GSI exhibited decreased Hes5, Hes7, Hey2, and HeyL expression in bone, but not in brain or gut, compared to vehicle-treated mice.
Figure 2B:
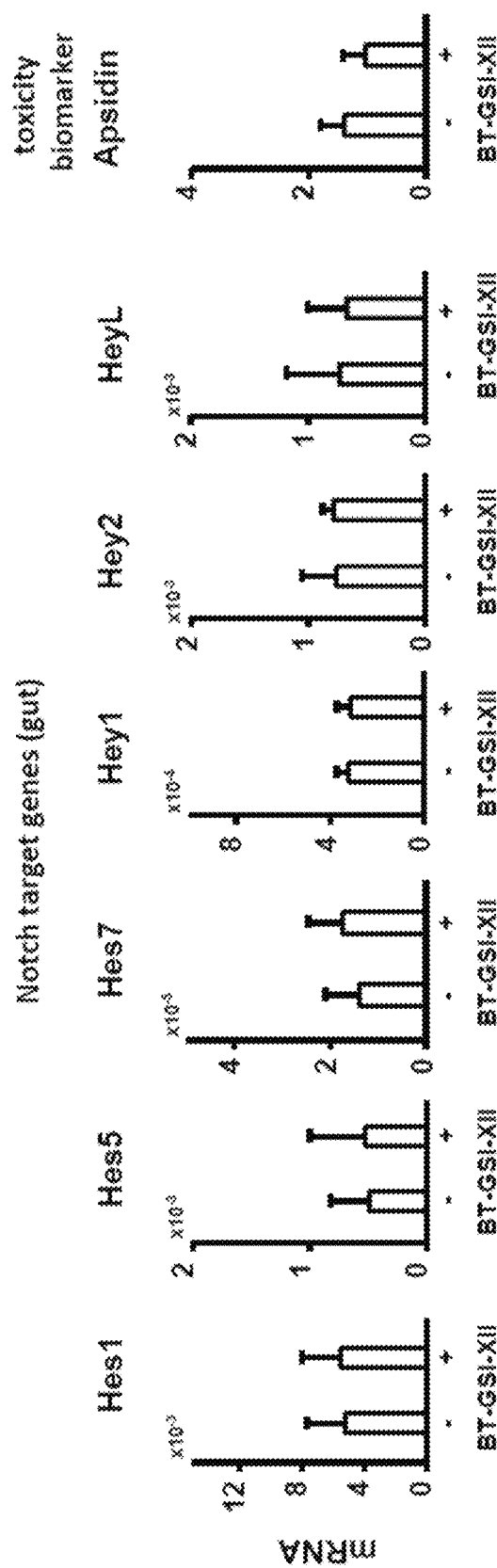
FIG. 2B. Graphs illustrating the effect on Notch target genes. Mice treated with BT-GSI exhibited decreased Hes5, Hes7, Hey2, and HeyL expression in bone, but not in brain or gut, compared to vehicle-treated mice. Further, BT-GSI-XII did not increase the expression in the gut of Apsidin, a biomarker of gastrointestinal toxicity.
Figure 5:
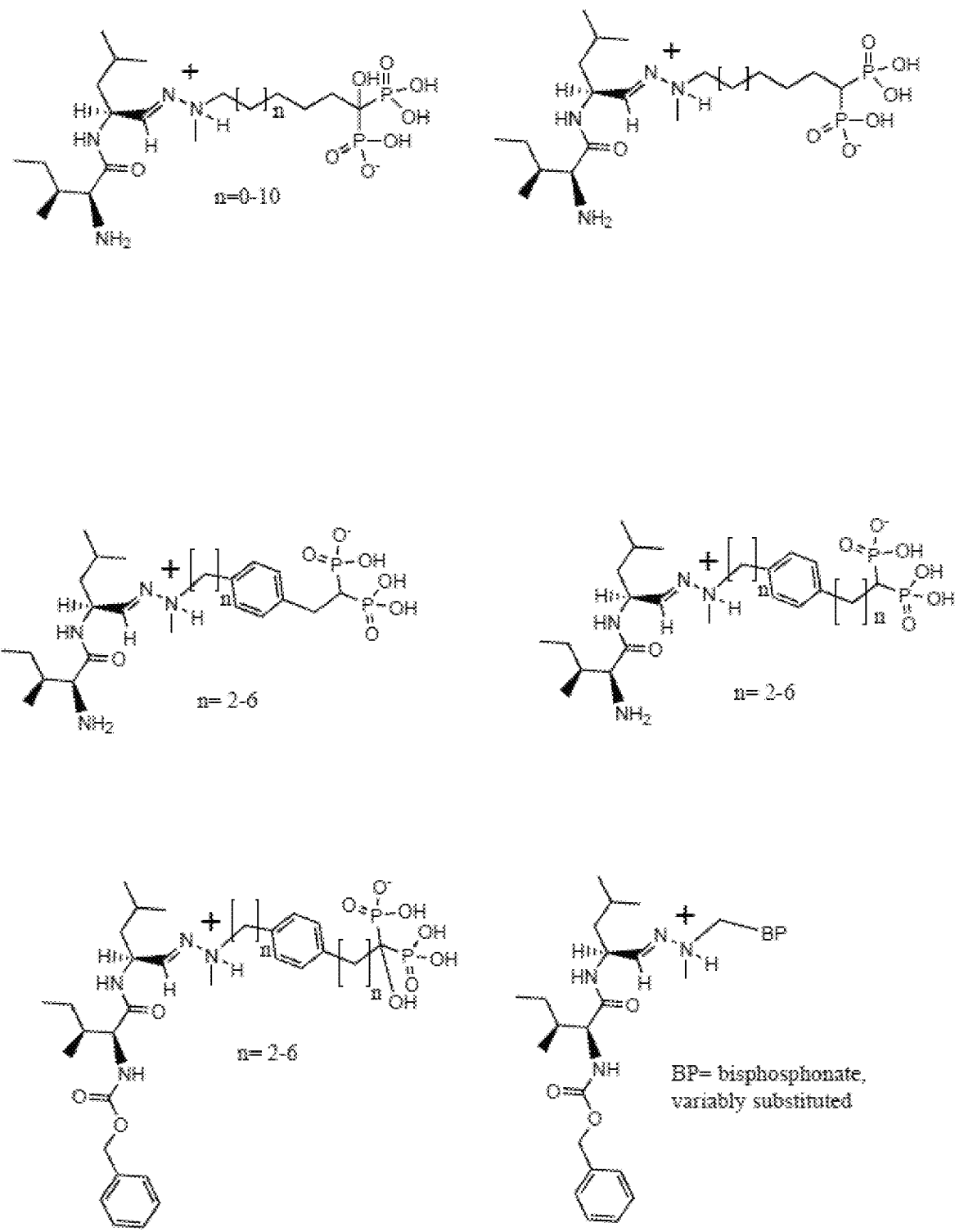
FIG. 5. Exemplary structural formula of some of UR-15 analogs.
Figure 6:
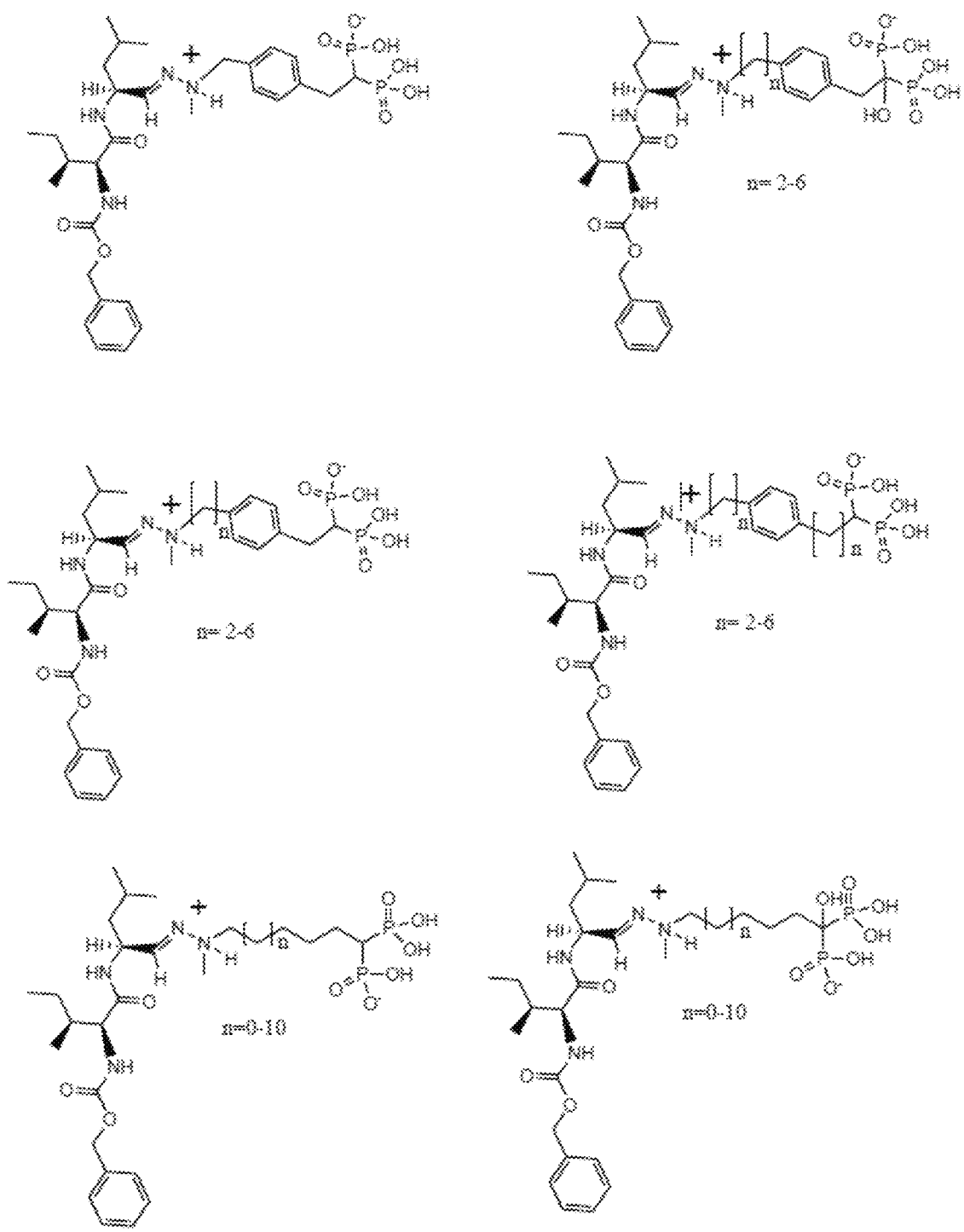
FIG. 6. Exemplary structural formula of some of UR-15 analogs.
Figure 7:
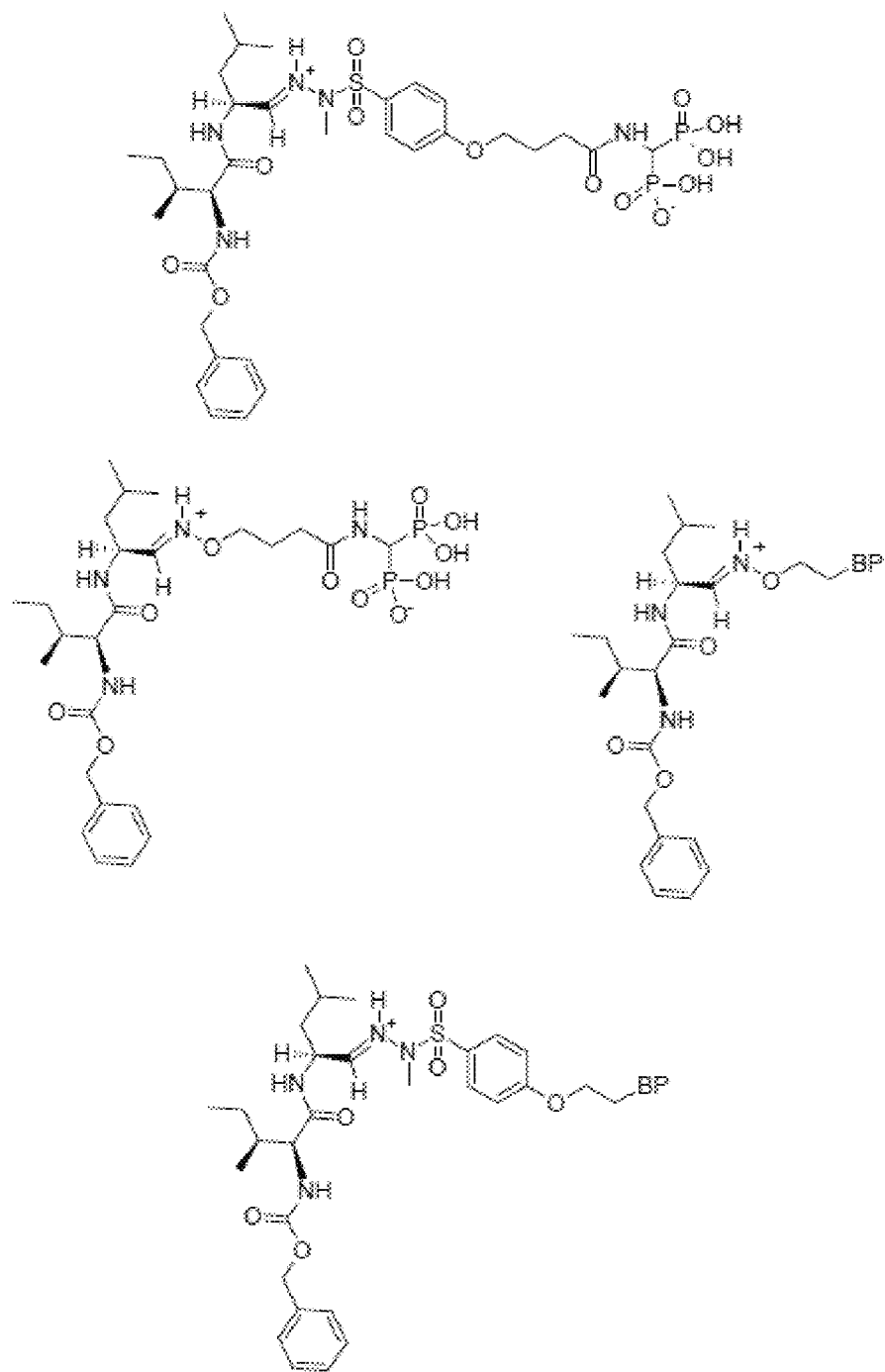
FIG. 7. Exemplary structural formula of some of UR-15 analogs.
Figure 8:
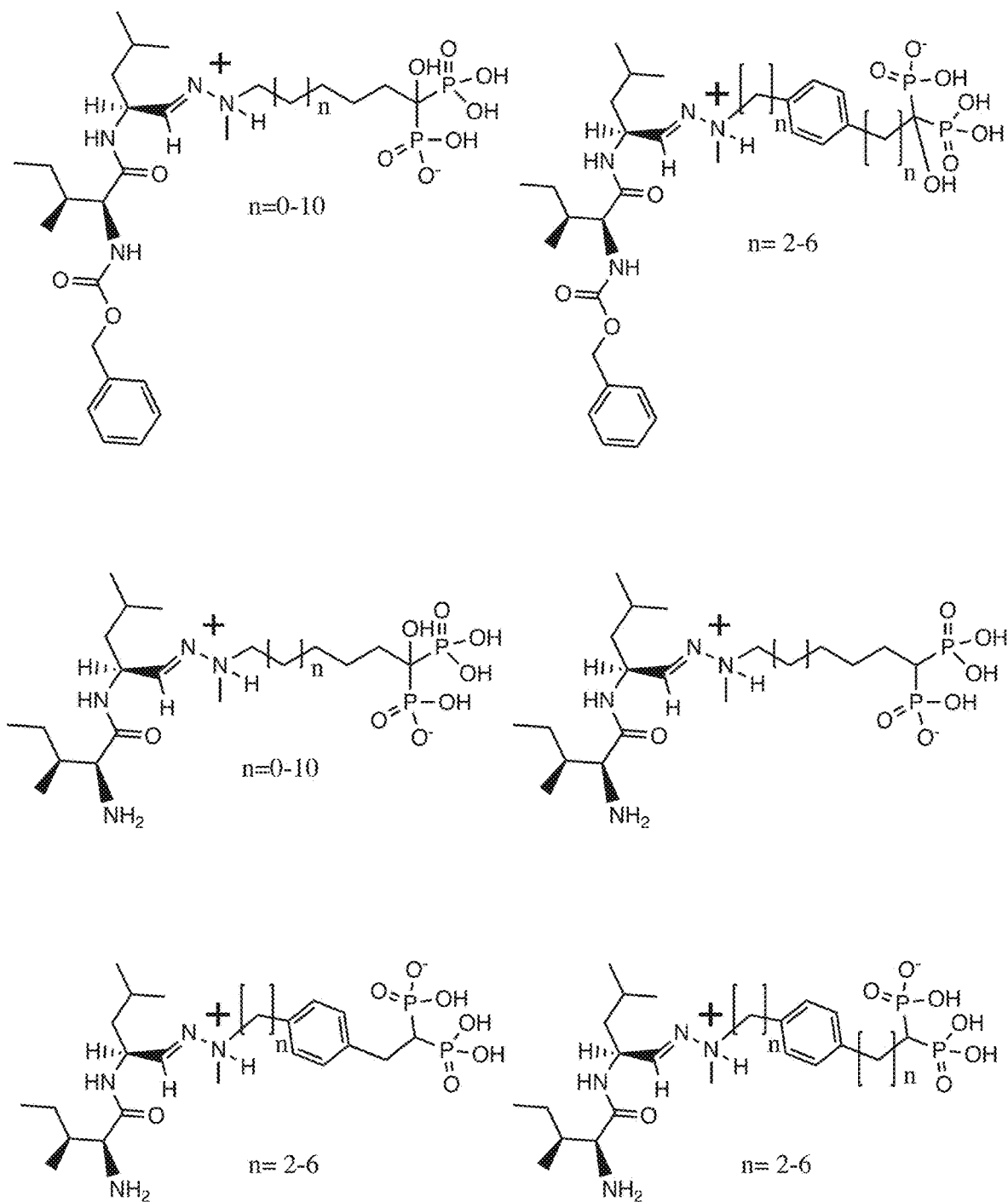
FIG. 8. Exemplary structural formula of some of UR-15 analogs.
Figure 9:
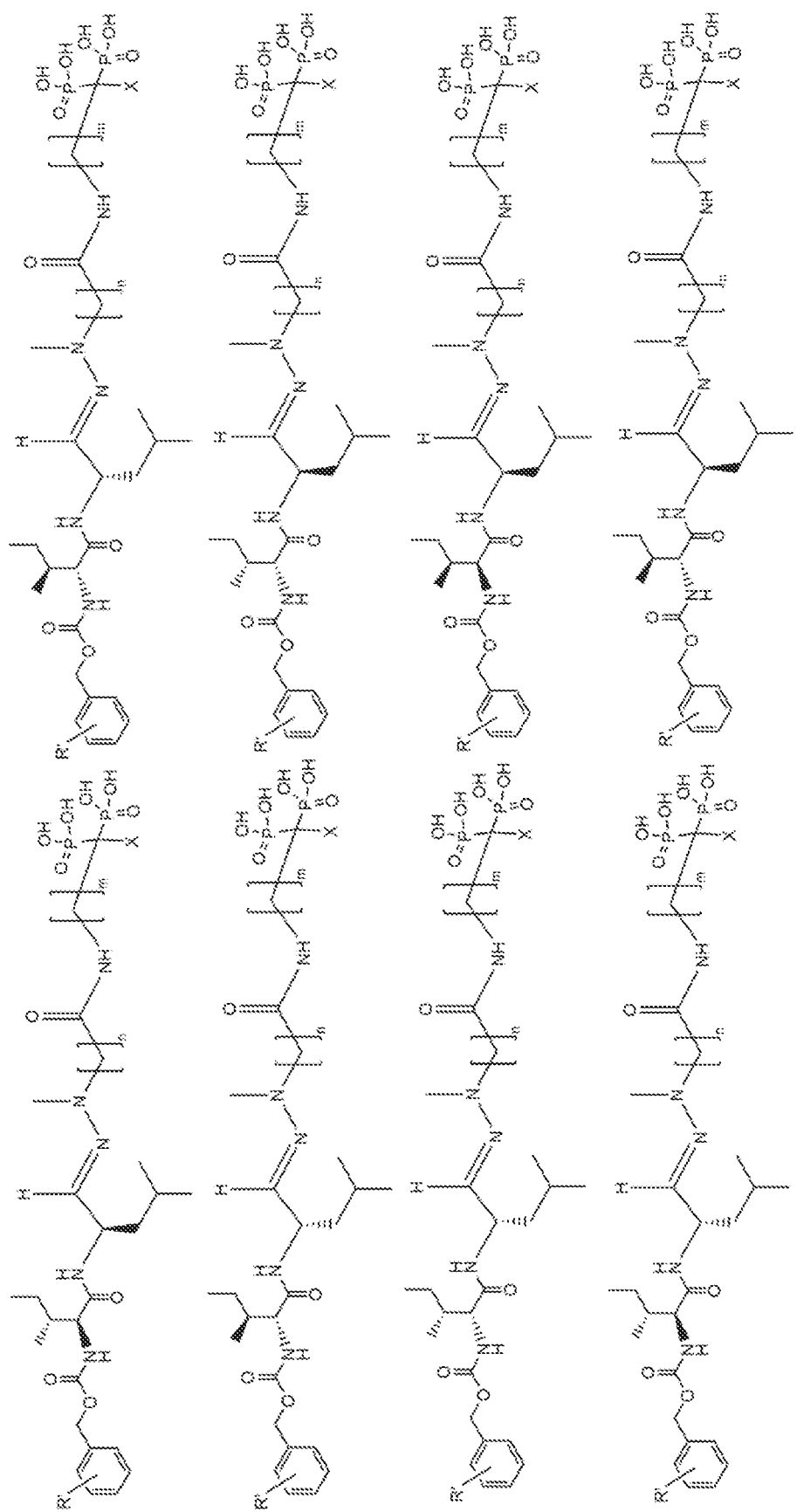
FIG. 9. Exemplary structural formula of some of stereoisomers.

Referring now to FIG. 1A, the control unconjugated GSI decreased Notch target gene expression (Hes1) in 5TGM1 myeloma cells, but BT-GSI-XII had no effect in vitro. However, when both GSI-XII and BT-GSI-XII were pre-incubated at low pH to mimic the acidic conditions in resorption sites, equal inhibition of Notch target gene expression was observed in myeloma cells (FIG. 1B). Referring now to FIG. 1C, ex vivo, both GSI-XII and BT-GSI-XII (non-pre-incubated) similarly decreased Hes1/5 expression in whole bone organ cultures that reproduce conditions present in the bone microenvironment. In vivo, administration of BT-GSI-XII (5 µg/g, 3×wk) to normal 4-month old female mice for 2 weeks was well tolerated and no skin issues were observed. Referring now to FIG. 1D, BT-GSI-XII treated mice exhibited higher total (3%), femoral (4%), and spinal (7%) BMD compared to control mice. BT-GSI-XII did not affect the circulating levels of the bone formation marker P1NP, but decreased serum CTX by 40%, a marker of bone resorption. (FIG. 1E). Referring now to FIG. 2, mice treated with BT-GSI exhibited decreased Hey2, Hes5, and Hes7 mRNA expression in whole bone preparations, but not in brain or gut, compared to vehicle-treated mice. Further, BT-GSI did not increase Apsidin expression in the gut, a biomarker of gastrointestinal toxicity. BT-GSI-treated mice had decreased serum levels of CTX (−40%), a bone resorption marker, and upregulated Opg mRNA expression in bone, thereby decreasing the Rankl/Opg ratio (FIG. 3). Consistent with these findings, BT-GSI-XII treated mice exhibited a 50% decreased in the bone surface covered by osteoclasts compared to control mice. BT-GSI-XII treated mice exhibited higher total (+3%), femoral (+4%), and spinal (+7%) BMD compared to control mice. Further, microCT analysis revealed that mice receiving BT-GSI-XII had increased cancellous bone volume (+25%) and trabecular thickness (+10%) compared to vehicle-treated mice. Serum levels of the bone formation marker P1NP, bone formation and mineral apposition rates, number of osteoblasts, and the expression of osteoblast markers, including Wnt target genes and the osteocyte-derived Sost/Sclerostin remained unchanged by BT-GSI-XII.

Taken together, these findings appear to demonstrate that BT-GSIs (e.g., BT-GSI-XII) induce bone specific Notch inhibition, reduce osteoclast formation without affecting osteoblast activity, and lacks gut toxicity. Further, a BT-GSI can circumvent the deleterious side effects that limit the use of this class of inhibitors. Further, BT-GSIs inhibit bone resorption and favors bone gain. Thus, BT-GSI can be a promising approach to inhibit the growth of myeloma cells and improve skeletal disease in myeloma patients by inhibiting resorption.

Daily injections of PTH (iPTH) are thought to cause bone anabolism by increasing osteoblast number and function. However, iPTH can also increase bone resorption, which can limit bone gain. iPTH activates Notch signaling in osteocytes; and bone-targeted Notch inhibition using a γ-secretase inhibitor (GSI) conjugated to an alendronate-modified bone-targeting molecule (BT-GSI) decreases Notch signaling in bone, and reduces CTX (−40%) while preserving bone formation, leading to increases in BMD (4-7%) and cancellous bone volume (BV/TV; 30%).

Figure 10A:
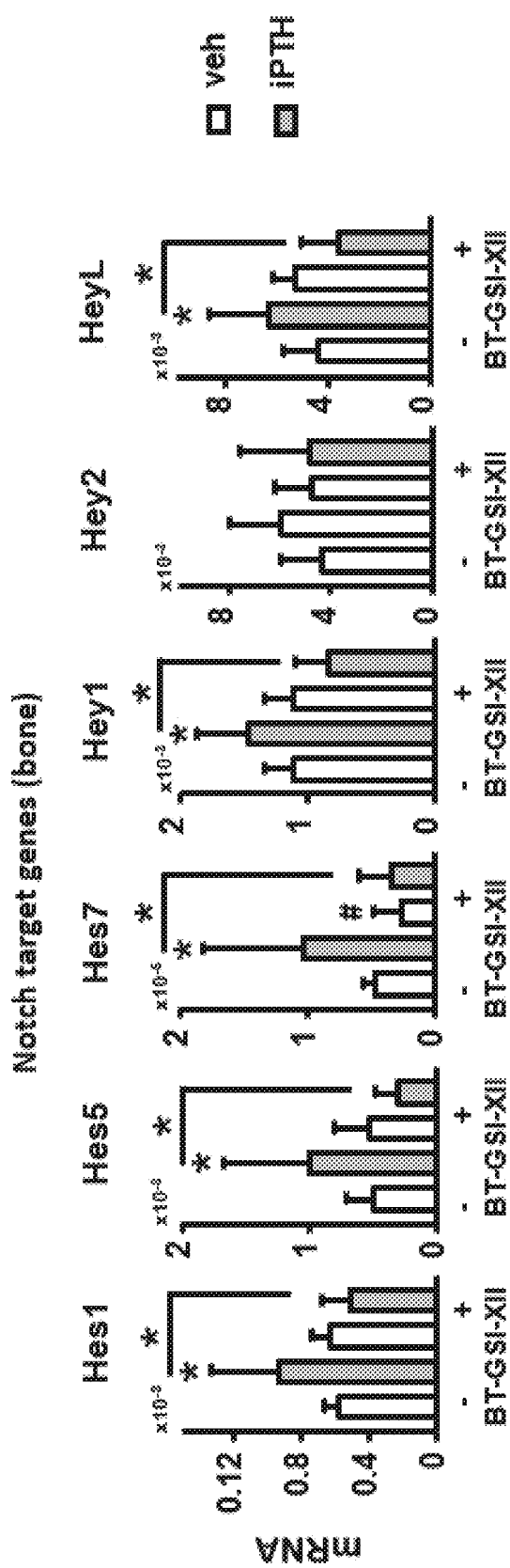
FIG. 10A. Graphs illustrating the effect of daily injections of PTH (iPTH) and BT-GSI-XII on Notch target gene expression in bone.
Figure 10B:
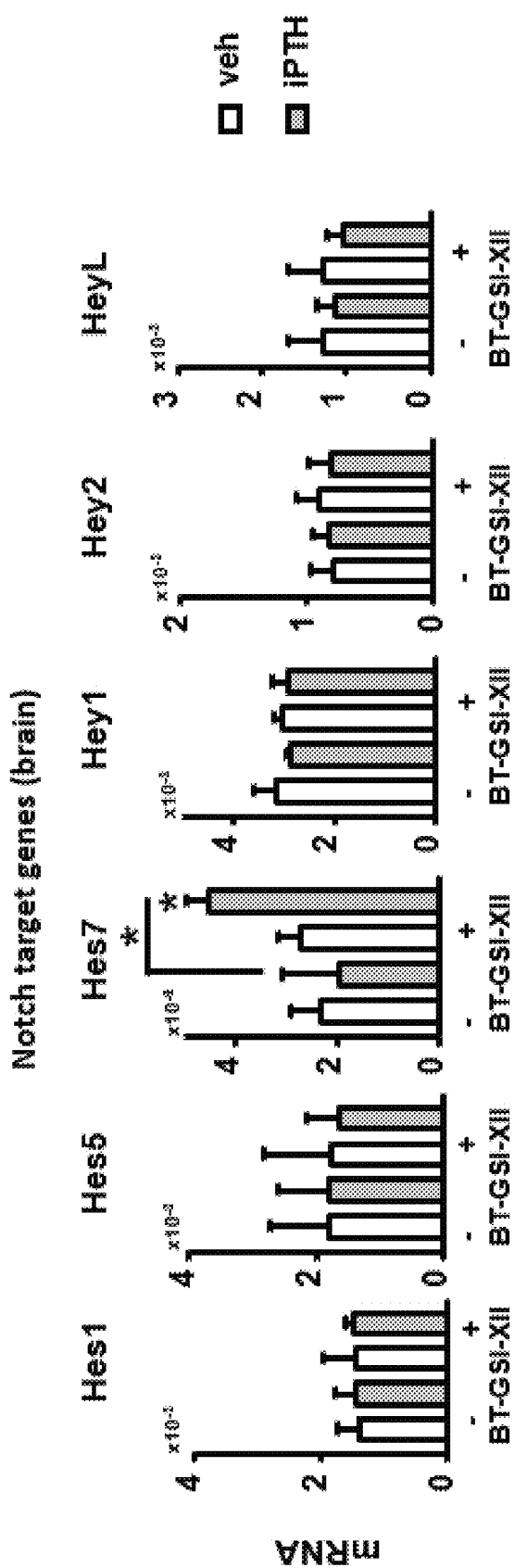
FIG. 10B. Graphs illustrating the effect of daily injections of PTH (iPTH) and BT-GSI-XII on Notch target gene expression in brain.
Figure 10C:
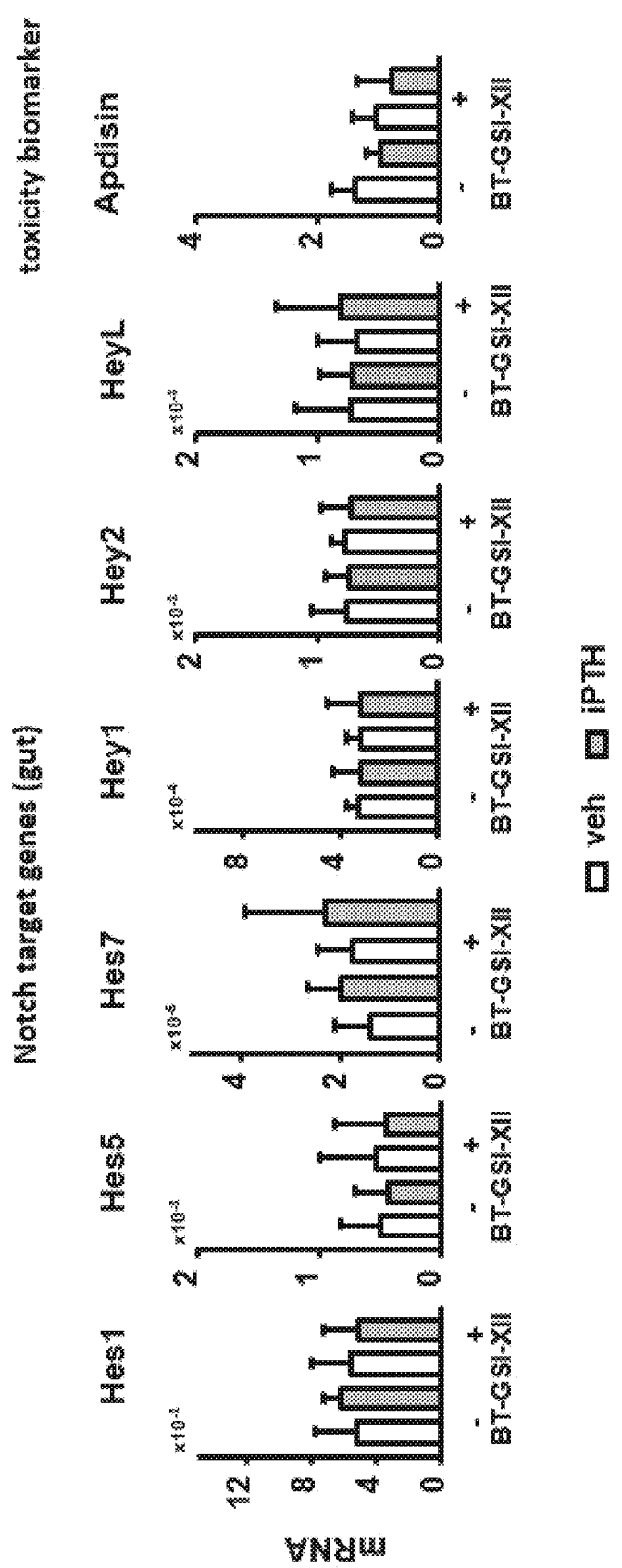
FIG. 10C. Graphs illustrating the effect of daily injections of PTH (iPTH) and BT-GSI-XII on Notch target gene expression in gut.
Figure 11:
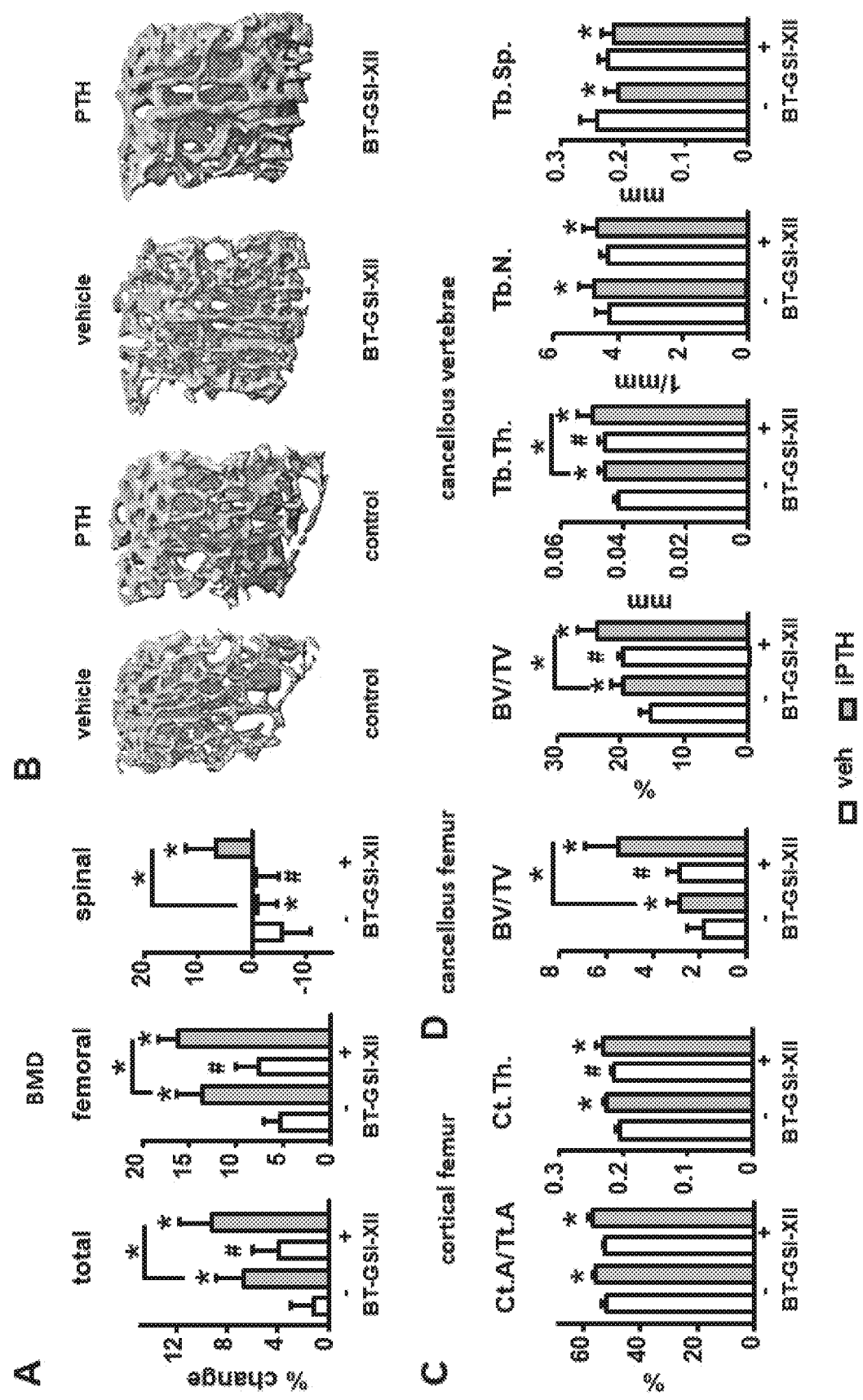
FIG. 11A. Graphs illustrating the effect of daily injections of PTH (iPTH) and BT-GSI-XII on Bone Mineral Density (BMD).
FIG. 11B. Pictures illustrating the effect of daily injections of PTH (iPTH) and BT-GSI-XII on bone mass.
FIG. 11C. Graphs illustrating the effect of daily injections of PTH (iPTH) and BT-GSI-XII on cortical area fraction (Ct.A/Tt.A) and cortical thickness (Ct.Th.).
FIG. 11D. Graphs illustrating the effect of daily injections of PTH (iPTH) and BT-GSI-XII on bone volume fraction (BV/TV), trabecular thickness (Tb.Th.), trabecular number (Tb.N.), and trabecular spacing (Tb. Sp) in cancellous femur and/or in cancellous vertebrae.

To investigate whether a combination of iPTH (anabolic) and BT-GSI (anti-catabolic) increases bone mass to a higher extent than either agent alone, BT-GSI (5 mg/kg, 3×/wk) or saline was co-administered with iPTH (100 ng/g/day) or vehicle for 2 wks to 4-mo-old mice (n=10/group). Referring now to FIG. 10, iPTH increased expression of the Notch target genes Hes1/5/7 and Hey1/L in bone, and co-administration of BT-GSI decreased the iPTH-induced elevated expression of Hes1/5/7 and Hey1/L to a level comparable to the control mice receiving vehicle injections (FIG. 10A). The expression of Notch target genes in brain or gut remained unchanged by either iPTH, BT-GSI, or the combination (FIGS. 10B and 10C) iPTH increased total (7%) and femoral (13%), and preserved spinal BMD (0%); and co-administration of BT-GSI potentiated the increase at all bone sites (10, 17, and 7%, respectively) (FIG. 11). Co-administration of BT-GSI exhibited additional 25% increase in cancellous BV/TV (L4 and distal femur) and trabecular thickness when compared to the iPTH-induced increase. However, the co-administration of BT-GSI did not alter the iPTH-induced increase in cortical bone area (8%).

Figure 13E:
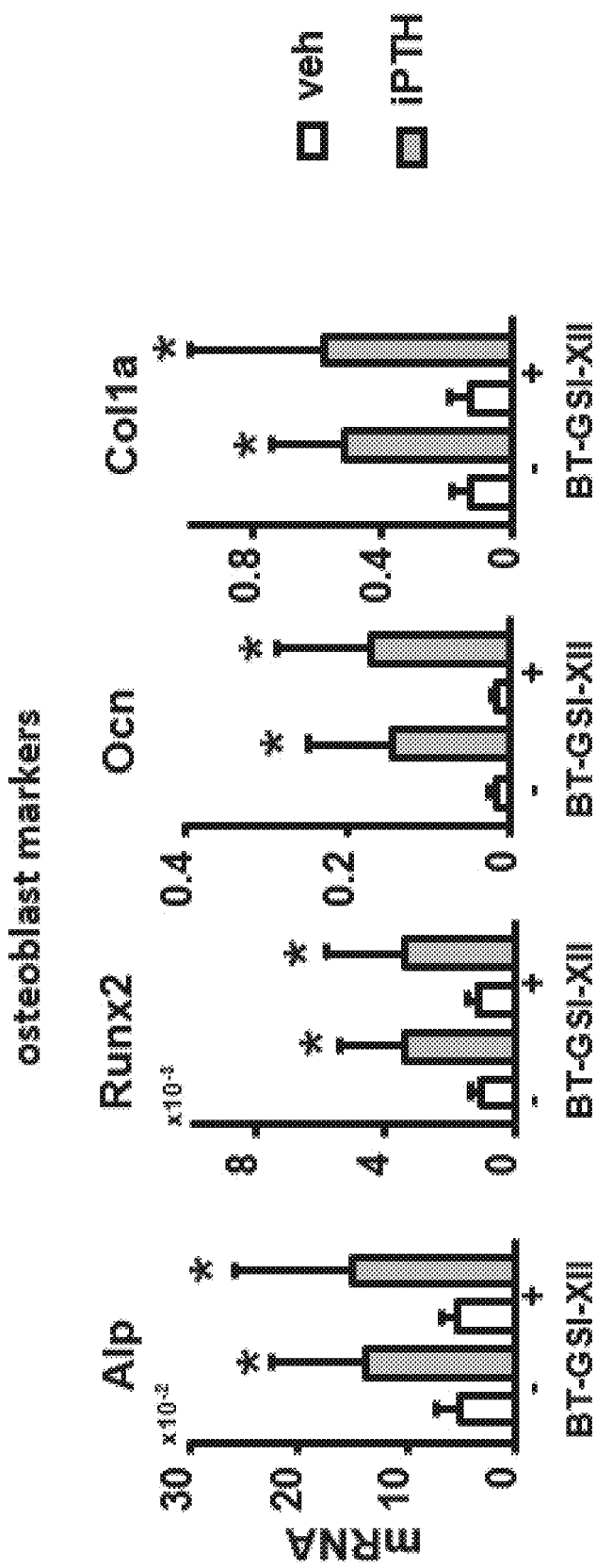
FIG. 13E. Graphs illustrating the effect of daily injections of PTH (iPTH) and BT-GSI-XII on the level of osteoblast markers.

Referring to FIG. 12, co-administration of BT-GSI decreased iPTH-induced elevated serum CTX (30%) and osteoclast number/surface (25%) levels to the values that are less than those exhibited in control mice receiving vehicle (FIG. 12A-B). The iPTH-induced elevated Rankl/Opg expression ratio in bone (1.5-fold) remained unchanged by the co-administration of BT-GSI (FIG. 12C). No changes were found in M-Csf expression. Additionally, unconjugated GSI reduced Rankl-induced osteoclast differentiation in vitro with an $EC_{50}$~0.1 µM (FIG. 12D). Further, the bone-targeting molecule alone required a dose 10 times higher than GSI to decreased osteoclastogenesis. Referring now to FIG. 13, co-administration of BT-GSI decreased iPTH-induced elevated serum P1NP (e.g., about 30% decrease); however, the co-administration of BT-GSI maintained the iPTH-induced elevated bone formation rate (20%) and osteoblast number/surface (20%) in cancellous bone (FIG. 13B-C). Further, mice receiving iPTH alone or combined with BT-GSI induced elevated mRNA levels of Alp1, Runx2, Bglap, and Wnt target genes, and reduced mRNA level of Sost in bone (FIG. 13 D-E).

These results demonstrate that bone-targeted inhibition of the Notch pathway in the frame of anabolic PTH signaling induces a superior bone gain compared to individual treatments and provide the bases for novel therapeutic strategies that reduce bone catabolism while simultaneously preserve bone anabolism.

While the novel technology has been illustrated and described in detail in the figures and foregoing description, the same is to be considered as illustrative and not restrictive in character, it being understood that only the preferred embodiments have been shown and described and that all changes and modifications that come within the spirit of the novel technology are desired to be protected. As well, while the novel technology was illustrated using specific examples, theoretical arguments, accounts, and illustrations, these illustrations and the accompanying discussion should by no means be interpreted as limiting the technology. All patents, patent applications, and references to texts, scientific treatises, publications, and the like referenced in this application are incorporated herein by reference in their entirety to the extent they are not inconsistent with the explicit teachings of this specification.

We claim:
1. A compound, comprising:

A-Y—B, wherein:
A is

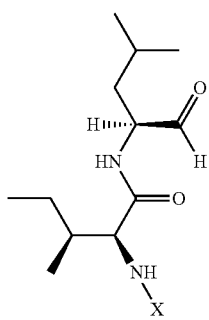

and X is selected from the group consisting of: H and

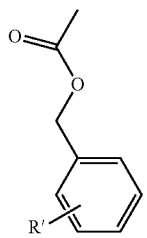

Y is a linker of formula $NR_1$;
R' is H, $CH_3$, alkyl, halogen, $CF_3$, CN, OH, $OCH_3$, or O-alkyl;
wherein $R_1$ is $NR_2R_3$, $NR_2S(=O)_2R_3$ or $R_2OR_3$;
$R_2$ and $R_3$ are independently selected from H, $C_1$-$C_{10}$ alkyl, $C_1$-$C_{10}$ alkoxy, $C_6H_5OR_4$, and wherein $R_2$ and $R_3$ are not both H,
$R_4$ is $C_1$-$C_{10}$ alkyl, $C_1$-$C_{10}$ alkoxy, carbonyl, or amide; and
B is at least one bisphosphonate optionally substituted with OH, halogen, $CH_3$, $NH_2$,
or a pharmaceutically acceptable salt thereof.

2. A compound comprising one or more stereoisomers of the formula:

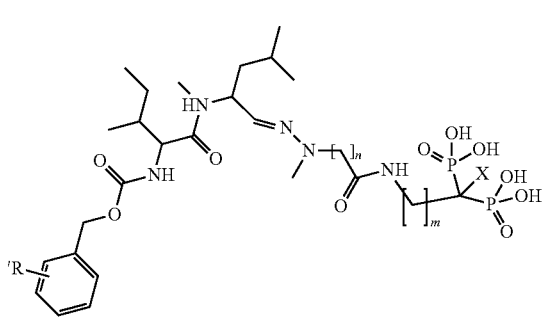

wherein:
'R is H, $CH_3$, alkyl, halogen, $CF_3$, CN, OH, $OCH_3$, or O-alkyl;
n is 1-9;
m is 0-7; and
X is H, OH, halogen, $CH_3$, $NH_2$, N-alkyl, or N-dialkyl;
or a pharmaceutically acceptable salt.

3. The compound according to claim 2, wherein n is 1-3, m is 0, and X is H.

4. A compound of the formula:

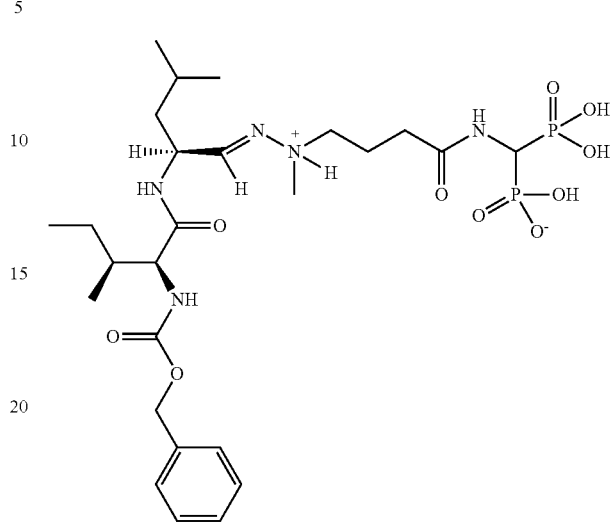

or a pharmaceutically acceptable salt thereof.

5. The compound according to according to claim 2, wherein the one or more stereoisomers comprise any one or more of the formula:

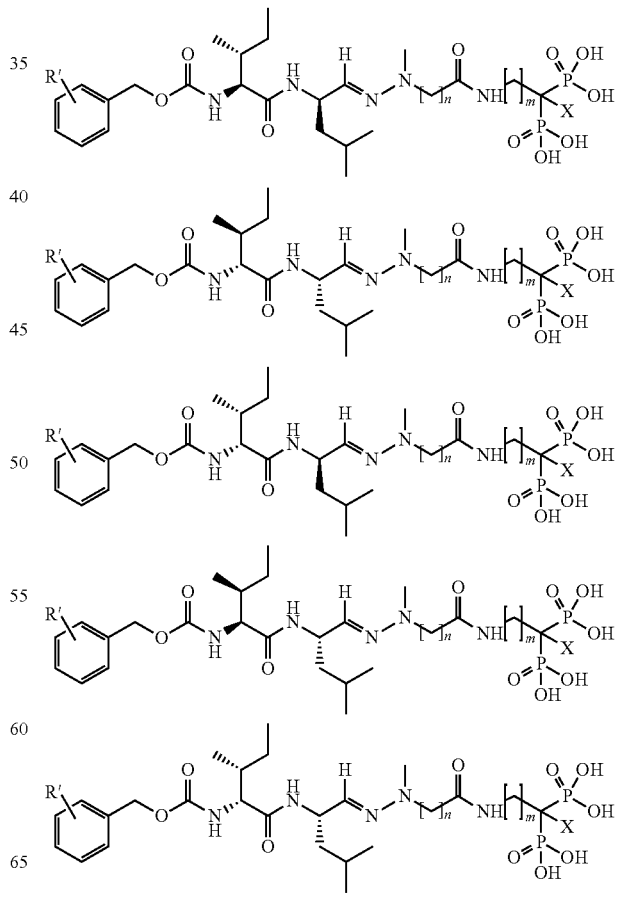

-continued
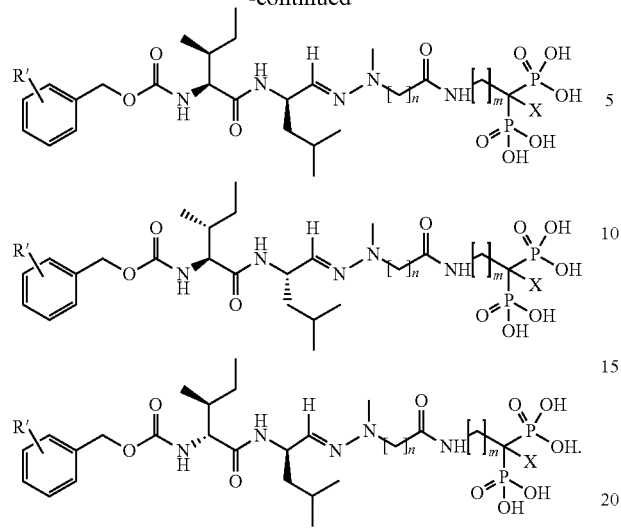
* * * * *